United States Patent
Yoshikawa et al.

(10) Patent No.: US 7,333,718 B2
(45) Date of Patent: *Feb. 19, 2008

(54) WORK DATA COLLECTION METHOD

(75) Inventors: Takeshi Yoshikawa, Kanagawa (JP);
Koichi Takahashi, Kanagawa (JP);
Masaya Kaneko, Kanagawa (JP); Yuko Endo, Kanagawa (JP); Yoshio Obara, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1283 days.

This patent is subject to a terminal disclaimer.

(21) Appl. No.: 10/107,823

(22) Filed: Mar. 28, 2002

(65) Prior Publication Data

US 2003/0043266 A1 Mar. 6, 2003

(30) Foreign Application Priority Data

Mar. 28, 2001 (JP) .............................. 2001-093895

(51) Int. Cl.
*H04N 5/91* (2006.01)
*G06F 19/00* (2006.01)
(52) U.S. Cl. ......................... 386/95; 386/46; 700/108
(58) Field of Classification Search ................. 386/46, 386/52, 55, 68, 81, 83, 95, 111, 121; 358/93, 358/101, 183, 903; 725/37, 60–61, 105, 725/114–115, 133, 141, 153; 700/108–111; 348/39, 61, 115, 121
See application file for complete search history.

(56) References Cited

U.S. PATENT DOCUMENTS

| 4,413,277 | A |   | 11/1983 | Murray |         |
|-----------|---|---|---------|--------|---------|
| 5,905,525 | A | * | 5/1999  | Ishibashi et al. | 348/39 |
| 5,917,990 | A | * | 6/1999  | Zamara et al. | 386/95 |
| 7,111,317 | B1 | * | 9/2006 | McIntyre et al. | 725/105 |

FOREIGN PATENT DOCUMENTS

WO    WO 99/46664 A2    9/1999

* cited by examiner

*Primary Examiner*—Thai Q. Tran
*Assistant Examiner*—Mishawn Dunn
(74) *Attorney, Agent, or Firm*—Sughrue Mion, PLLC

(57) ABSTRACT

Biological data obtained through observation devices and job titles are recorded on a data recording device in association with time data that are generated at regular intervals. A data processing computer produces a graph from the data read out from the data recording device. The observation devices, the data recording device and the data processing computer are connected to a network, so that a required graph may be produced by processing data at a place remote from the observatory.

37 Claims, 18 Drawing Sheets

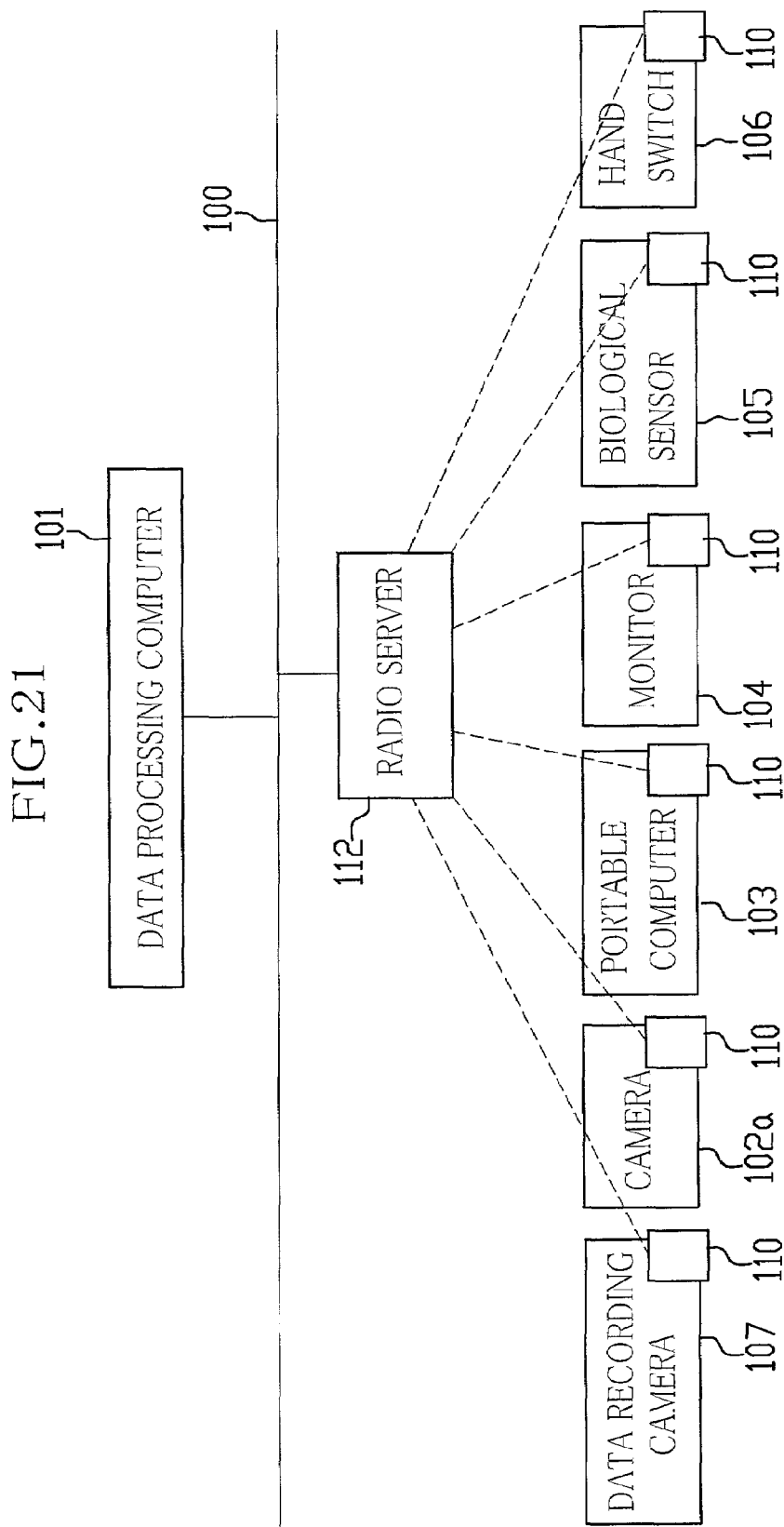

WORK DATA COLLECTION METHOD

BACKGROUND OF THE INVENTION

1. Field of the Invention

The present invention relates to a work data collection method, by which data on working conditions, especially data of workload on the worker, may be collected either in a light room or in a darkroom, and more may be collected.

2. Background Arts

It is conventional to collect data on the existing working conditions in a workplace, to make analysis based on the work data for the sake of improving work efficiency. A lot of methods have been developed for collecting the work data. The most primitive method is handwriting the work data on a note book, and thereafter inputting the work data in a data processing computer with reference to the note book . This method is apparently inefficient.

As a recent work data collection method, a data collector uses a bar code sheet having bar codes representative of job titles printed thereon, and reads a job title by scanning a corresponding one of the bar codes through a handy bar code reader at the start of a corresponding job in a workplace. At the end of that job, the data collector scans one of the bar codes that represents an end of job. The bar code reader has a clock and a memory incorporated therein, so the time when the bar code of the job title is scanned is recorded as a job start time on the memory, and the time when the bar code of the job end is scanned is recorded as a job end time on the memory. The data collector repeats scanning the bar codes at the start and end of each job in the same way, to record the job titles and the start and end times of the respective jobs in the memory of the bar code reader.

After collecting the work data in the workplace, the bar code reader is connected to a personal computer, to transfer the work data from the memory of the bar code reader to the personal computer. On the personal computer, the work data is monitored and, if necessary, corrected, or some data is added to the work data. Then, the work data is processed and analyzed for displaying results of analysis in the form of tables and graphs on the personal computer. If necessary, the results are printed out as hard copies.

On the other hand, there is a device for collecting and storing data of a biological factor of a person through a specific sensor, hereinafter called a biological sensor, continuously or at regular intervals. This biological data collecting device has often been used for collecting biological data in examining a training program for an athlete. In that case, the biological sensors are put on the athlete's body while the athlete is exercising according to the training program. After the athlete works out the training program, the biological data collecting device is connected to a personal computer, to transfer the stored biological data to the personal computer. On the personal computer, the biological data is statistically processed to analyze loads on the athlete during the exercise on the basis of a change of the biological factor with the time and other data like this.

The above described work data collection methods are usable for those cases where the jobs are done in a light room. But where the jobs are done in a darkroom, e.g. on dealing with photographic film, the above described work data collection methods are inconvenient. Because darkroom glasses or goggles are needed for observation in the darkroom, and the darkroom goggles make it hard to see things in hand clearly, it is difficult to scan the bar code on the bar code sheet or read the time on a wrist watch in the darkroom. Also because any apparatus that emits light is not allowed in the darkroom, neither personal computer with a back-lit display panel nor any kinds of lighting devices are usable for work data collection in the darkroom.

The above described biological data collection method may be applicable to collecting biological data from the worker as data representative of workload on the worker during the jobs, because the workload affects work efficiency. However, this idea has not yet been incarnated but in a tentative stage.

SUMMARY OF THE INVENTION

In view of the foregoing, an object of the present invention is to provide a work data collection method that is applicable to collecting work data in the darkroom as well as in the light room.

Another object of the present invention is to provide a work data collection method by which workload data is collectable.

According to an aspect of the present invention, a work data collection method comprises the steps of photographing a series of different jobs done by at least a worker through a video camera, to take video signals of the jobs; recording video signals of said jobs while recording time signals generated at predetermined fixed intervals; inputting a break point signal in the video camera at each break point between the jobs; and recording the break point signal on a memory device along with the video signal and a proximate one of the time signals that is representative of a time proximate to the break point.

Since the break point signal is recorded along with the video signal of the jobs, it is easy to search the break points between the jobs, i.e. cue up the video signal at each break point, by use of the break point signal. Using an infrared video camera as the video camera makes it possible to collect work data of those jobs done in a darkroom.

According to another aspect of the present invention, a work data collection method comprises the steps of photographing a series of different jobs done by at least a worker through a video camera, to take a video signal of the jobs; recording the video signal on a memory device through a personal computer while recording time signals generated at predetermined fixed intervals; inputting a break point signal in the personal computer at each break point between the jobs; and recording the break point signal on the memory device along with the video signal and a proximate one of the time signals that is representative of a time proximate to the break point.

Since the break point signal is entered in the personal computer and is recorded along with the video signal of the jobs, it is unnecessary to convert the break point signal into data specific for the personal computer. Accordingly, data processing is simplified and speeded.

By measuring workload on the worker during at least one of the jobs; and recording the workload data on a memory device in association with the video signal and the break point signal, it becomes easy to provide data of the workloads during the respective jobs and examine the relationship between the workload and the contents or sequences of the jobs.

By measuring environmental factors around the worker during at least one of the jobs and recording data of the environmental factors on a memory device in association with the video signal and the break point signal, it becomes easy to provide data of the work environments and use it for improving the work environments.

It is preferable to input the break point signal as an image signal or a sound signal Then, it becomes easy to input the break point signal in the dark room as well as in the light room. By entering job titles in the video camera or the personal computer, the break points are completely correlated to the job titles. It is preferable to display job titles on a display device connected to a personal computer such that the display device is visible for a data collector while observing a series of different jobs done by at least a worker. Then the data collector may selects one of the displayed job titles through an input device connected to the personal computer, to enter job title data representative of the selected job title in the personal computer at each break point between the jobs.

According to still another aspect of the invention, a work data collection method comprising the steps of entering a job title as a sound signal through a microphone connected to a sound recording player having a clock function and a display section, at each break point between different jobs while the jobs are being sequentially done by at least a worker; recording the sound signal of the job title on a memory device of the sound recording player, along with data of an entrance time when the sound signal is entered, the entrance time being determined by the clock function of the sound recording player; and playing back a sound of the job title on the sound recording player, while displaying the entrance time of the played back job title on the display section. This method may be accomplished without bringing a video camera or a personal computer into the workplace.

Connecting observation devices, recording devices and a data processing computer through a network makes it possible to process data in a remote place from the observatory.

BRIEF DESCRIPTION OF THE DRAWINGS

The above and other objects and advantages of the present invention will become apparent from the following detailed description of the preferred embodiments when read in association with the accompanying drawings, which are given by way of illustration only and thus are not limiting the present invention. In the drawings, like reference numerals designate like or corresponding parts throughout the several views, and wherein:

FIG. 21 is an explanatory diagram illustrating an example of radio networking.

DETAILED DESCRIPTION OF THE EMBODIMENTS

Figure 1:
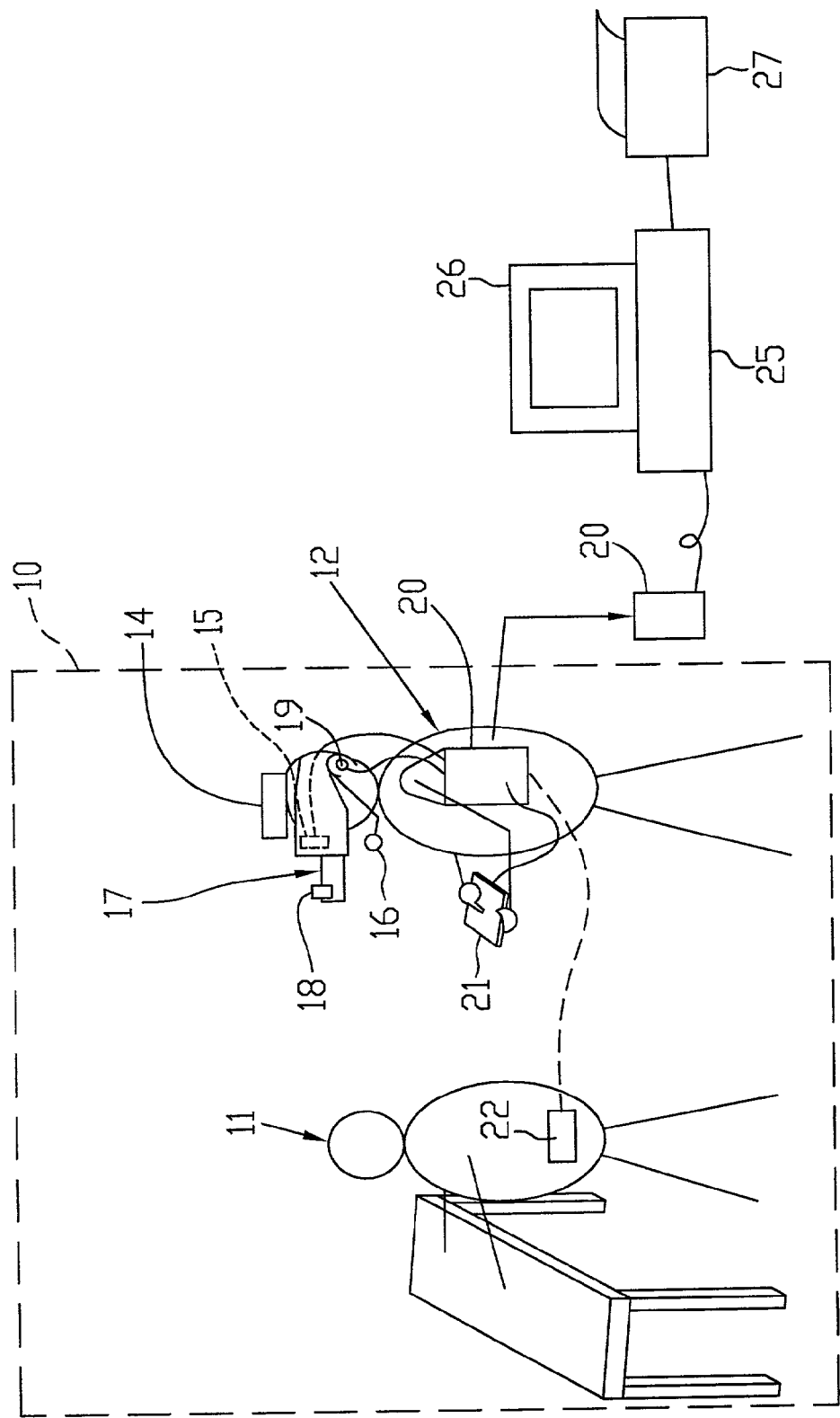
FIG. 1 is an explanatory diagram illustrating a work data collection method using a video camera and a portable personal computer, according to a first embodiment of the present invention.

In the first embodiment shown in FIG. 1, a data collector 12 who observes a worker 11 doing a job in a darkroom 10 has a very small infrared video camera 14, an LCD device 15 and a microphone 16 on his or her head. The sensitivity of the video camera 14 is set at an infrared range, i.e., a wavelength range from about 1000 nm to about 30,000 nm. The LCD device 15 is so positioned on the head that the data collector 12 may look up at a screen of the LCD device 15. In order to prevent leakage of back-light of the LCD display 15, the data collector 12 wears a pair of darkroom goggles 17 over the LCD display 15. The darkroom goggles 17 are well known in the art, and enable observing a faint optical image as a light optical image, so the data collector 12 can observe the job of the worker 11 in the darkroom 10.

It is preferable to install a plurality of such infrared video cameras in the darkroom 10. And more preferably, some or all of these cameras are provided with a zooming device and a device for turning the direction of the lens. It is also possible to install a console in a light room outside the darkroom 10, for the data collector 12 to operate the cameras while observing pictures photographed through the cameras, and enter titles and title codes of respective jobs done in the darkroom 10. This configuration helps the data collector in operation and data input. Instead of the LCD device 15, the data collector 12 may put on a display device which projects an image directly onto his retinas. This type of display device may have a smaller size than the LCD device 15. In addition, since the light is directed from the display device to the eyes of the data collector 12, leakage of the light is lessened. To minimize the light leakage, it is possible to provide a slit between the light projecting type display device and the eyes, or cover the display device with a shielding member.

To a forward protruding end of the darkroom goggle 17 is attached a work environment sensor 18 for measuring illuminance, noise, temperature, humidity and other environmental factors in the workplace. The data collector 12 also has an earphone 19 on his or her ear. The infrared video camera 14, the LCD display 15, the microphone 16, the work environment sensor 18 and the earphone 19 are connected to a portable personal computer 20 with an image recording function. Besides, a hand switch board 21 and a biological sensor 22 are connected to this portable personal computer 20. The data collector 12 carries the portable personal computer 20 on his or her shoulder.

The LCD display 15 displays pictures as photographed through the infrared video camera 14 in a real time fashion, or a list of titles of the job to observe, and a clock. The microphone 16 is used for entering unlisted job titles as sound signals. The ear phone 19 is for listening to acoustic responses from the portable personal computer 20 that is generated in response to some operations on the portable personal computer 20, e.g. an alarm e.g. an alarm given when the sound signals are not entered or the data is not recognized.

The hand switch board 21 is provided with a pointing device for pointing one of the job titles listed on the LCD display 15 with a cursor, an enter key for entering the job title as selected by the cursor, and a signal input button for inputting a break point signal. Upon the signal input button is operated, the break point signal is recorded along with video data of the photographed pictures on a hard disc of the portable personal computer 20. The break point signal is used as a cueing signal for cueing up the head of each video data that corresponds to one job, so the break point signal is a sequential signal recognizable for video players. For example, a mark or a sound that is recorded in the screen is used as the break point signal. Where the sound is used as the break point signal, the break point signal may be entered through the microphone 16.

In alternative, the command for switching over the pages on the LCD device 15, or the job titles or the job codes may be entered through the microphone 16 alone. In that case, the content entered as sound signals may be displayed on the LCD device 15, so that the data collector 12 may visually confirm the entered content. If the entered content is correct, the data collector 12 says "OK" to the microphone 16.

It is preferable to provide each device with a clock and adjust the clock to the real time, so that the respective apparatuses may start working at the same time, and that any of the collected data may be associated with time data. Thus the collected data may be matched with each other on the data processing. Where the sound signals are entered, it is preferable to enter the break point signals even when the data is not entered, or recognized. It is also preferable to configure the portable personal computer 20 to request for data-reentrance when the portable personal computer 20 does not receive or recognize any data. In that case, the time after the data-reentrance is not used, but the unconfirmed data-entrance of which data-reentrance is not confirmed immediately before the data-reentrance is confirmed is regarded as a break point signal, and is written along with the time. It is also possible to use a synchronized recording device for correlation.

The biological sensor 22 is an infrared sensor in this embodiment, that measures body temperature of the worker 11. Because the body temperature rises when the job is busy, the body temperature may be used as a measure of workload on the worker. The workload affects the degree of fatigue and the working efficiency of the worker.

In a light room, the data collector takes off the darkroom goggle 17, and replaces the infrared video camera 14 with a compact video camera whose sensitivity is set at a wavelength range of visible rays (about 400 nm to about 700 nm) for ordinary photography. In that case, the work environment sensor 18 is separated from the darkroom goggles 17, and is put on the head or another part of the data collector 12.

Figure 2:
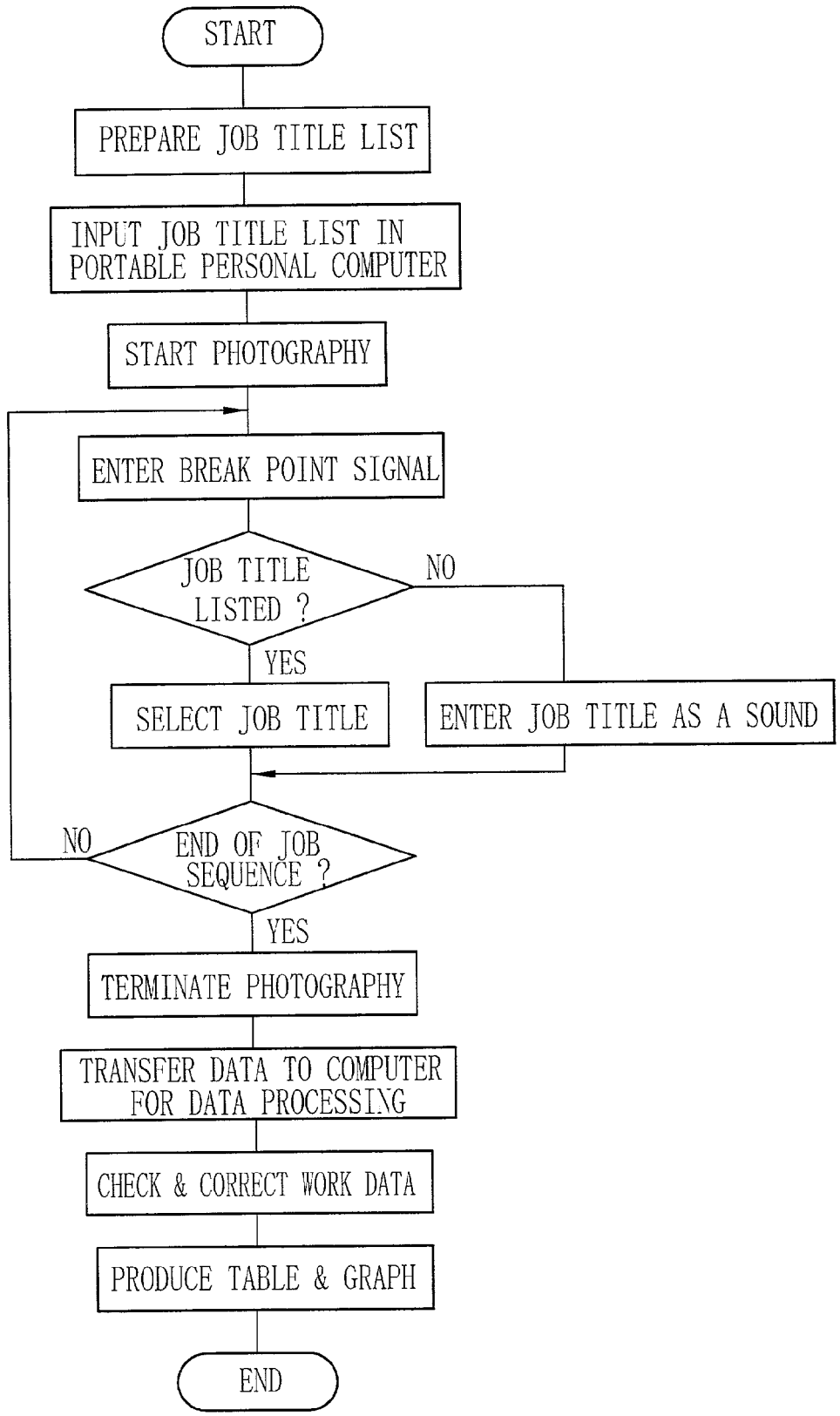
FIG. 2 is a flowchart illustrating a data collection sequence for the first embodiment.

Now the operation of the first embodiment will be described with reference to the flow chart of FIG. 2. Prior to the observation, the objects of the observation is specified, and the fineness of data to observe and other parameters are predetermined. As concrete exemplary of the objects of the observation, there would be redesigning the working process, or changing the number of workers disposed for the same job. Also the titles of jobs to observe are listed while defining the titles and classifying them according to some definition, and the job title list is input in the portable personal computer 20 in advance.

The data collector 12 first puts the portable personal computer 20 on the shoulder and the LCD display 15 on the head, and then puts on the darkroom goggle 17. Thereby, the LCD display 15 is covered with the darkroom goggle 17 in a light-tight fashion. Next, the data collector 12 puts the infrared video camera 14 on the head and the earphone 19 on the ear, and then turns on the portable personal computer 20. While holding the hand switch board 21 in the hand, the data collector 12 enters the darkroom 10.

In the darkroom 10, the worker 11 is doing a series of different jobs successively, whereas the data collector 12 observes through the darkroom goggle 17 the worker 11 doing the jobs, and starts photography by the infrared video camera 14 before the worker 11 starts the series of jobs. Simultaneously with the start of the initial job of the series, the data collector 12 inputs a first break point signal by operating the signal input button on the hand switch board 21.

Thereafter, the data collector 12 looks for the title of the job photographed at that time while having the job title list displayed on the LCD display 15. When there is the corresponding job title in the list, the data collector 12 operates the pointing device on the hand switch board 21 to place the cursor on that job title, and presses the enter key. Thus, the job title is recorded along with the video data on the hard disc of the portable personal computer 20. In this way, the data collector 12 photographs the jobs by the infrared video camera 14 while inputting the break point signal and the job title at each break point between the jobs, till all the jobs in the series are done. Among the break point signals, special signals may be used as the first and last ones to represent the initial and final jobs of the series respectively.

If the corresponding job title is not included in the job title list on the LCD display 15, the job title is entered as a sound signal through the microphone 16 at the break point for that job. The portable personal computer 20 converts the sound signal representative of the job title into character data and stores the character data along with the video data. As the infrared video camera 14 photographs the jobs, the work environment sensor 18 measures illuminance, noise, temperature and humidity of the workplace, and enters the measured values in the portable personal computer 20. The biological sensor 11 feeds data of the body temperature of the worker 11 in the portable personal computer 20. It is desirable to include "standby stage" in the job title list.

In the light room, the infrared video camera 14 is replaced with the ordinary compact video camera, the darkroom goggle 17 is taken off, and the work environment sensor 18 is removed from the darkroom goggle 17 and is put on the head of the data collector 12. Thereafter, the same operations are carried out as in the darkroom 10.

After the video data, the break point signals, the job title data, the work environment data, such as illuminance and noise, and the workload data are entered as work data with respect to all the jobs in one series, the portable personal computer 20 is connected through a cable to a personal computer 25 that is preset for data processing, and the work data is transferred from the portable personal computer 20 to the data processing personal computer 25. The work data may be transferred through a removable memory media, e.g. DVD (Digital Versatile Disc) and RAM.

The data processing personal computer 25 is used for monitoring the work data on a display 26, to correct or add necessary work data items. By retrieving the break point signals, the work data may be quickly played back at any break point between the jobs.

Since the time during which the infrared video camera 14 operates is recorded along with the video data in the portable personal computer 20, the work time taken for each individual job may be calculated based on the operation time of the infrared video camera 14. Thereafter, the work data is transformed into graphs or tables on the display 26, so as to make studies and analyses about the work data, e.g. about the relationship between the job content and the workload. If necessary, a hard copy of the work data is printed out through a printer 27.

It is possible to input the job titles in the data processing personal computer 25 after the photography is completed. In that case, the job titles may be entered in the data processing personal computer 25 through a keyboard or a bar code reader that is connected to the data processing personal computer 25 and is combined with a previously prepared bar code sheet having a plurality of bar codes representative of the job titles. This configuration permits recording the job titles while monitoring the photographed pictures, so it is applicable to those cases where there are a large number of different kinds of jobs, or the contents of the jobs are difficult to recognize or discriminate, or it is difficult to select and enter the job title while observing the job, for example where the work time for the job is very short.

It is also possible to record the video data in an ordinary digital video recorder instead of the portable personal computer. In that case, the break point signals are also recorded on the memory medium incorporated into or attached to the digital video recorder.

Figure 3:
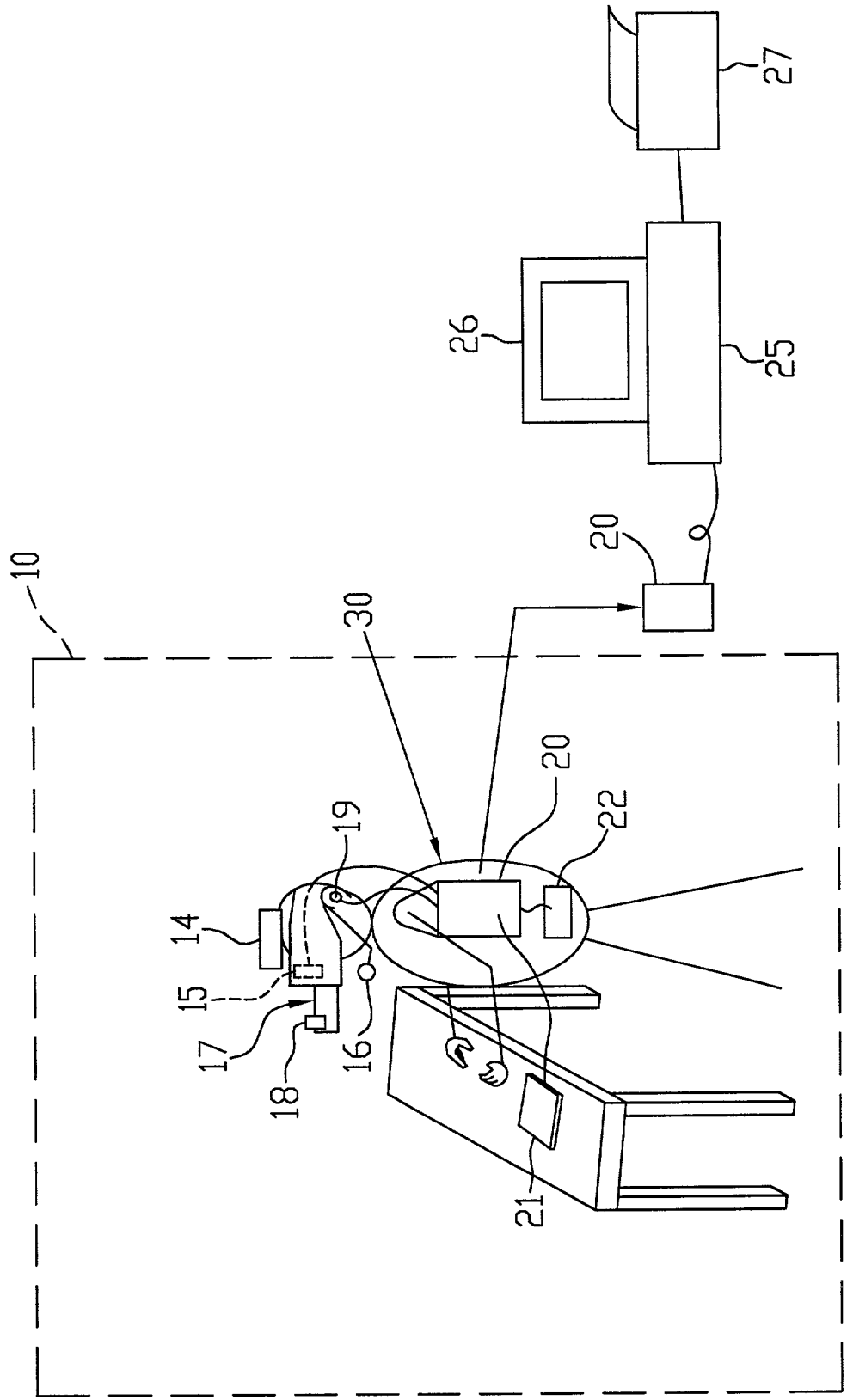
FIG. 3 is an explanatory diagram illustrating a second embodiment of the present invention, where a worker doubles as a data collector.
Figure 4:
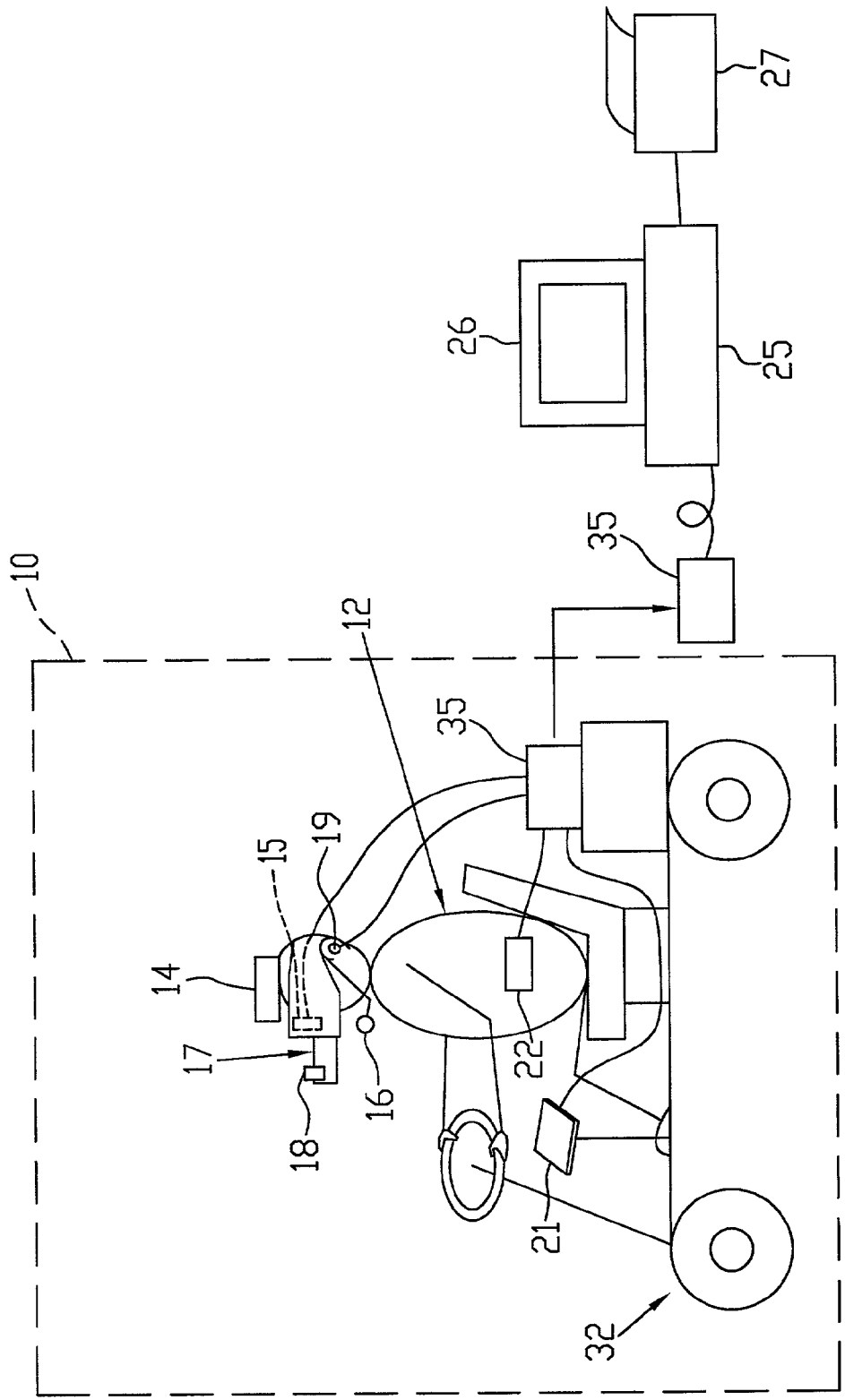
FIG. 4 is an explanatory diagram illustrating another embodiment of the present invention, where a data collector rides on a small car.

FIG. 3 shows a second embodiment where a worker doubles as a work data collector 30, and carries the same devices, including the infrared video camera 14, the LCD display 15 and the portable personal computer 20, as the data collector 12 in the first embodiment. In that case, a sensor for measuring perspiration may be used as the biological sensor 22, in addition to or instead of the body temperature sensor that is used for measuring the body temperature of the worker or work data collector 30.

Where the data collector 12 is supposed to move around on a small electric car 32, a personal computer 35 installed in the car 32 may be used in place of the portable personal computer 20. It is possible to carry a video camera with a higher performance on the car instead of the compact video camera 14 on the head. It is also possible to use an automatic vehicle that carries the personal computer and other machines and moves along with the data collector 12. In the first and the present and following embodiments, the data collector may collect the work data in those workplaces where a plurality of workers cooperate. Also, in the following embodiments, the workers themselves can double as the work data collectors, like in the second embodiment.

Figure 5:
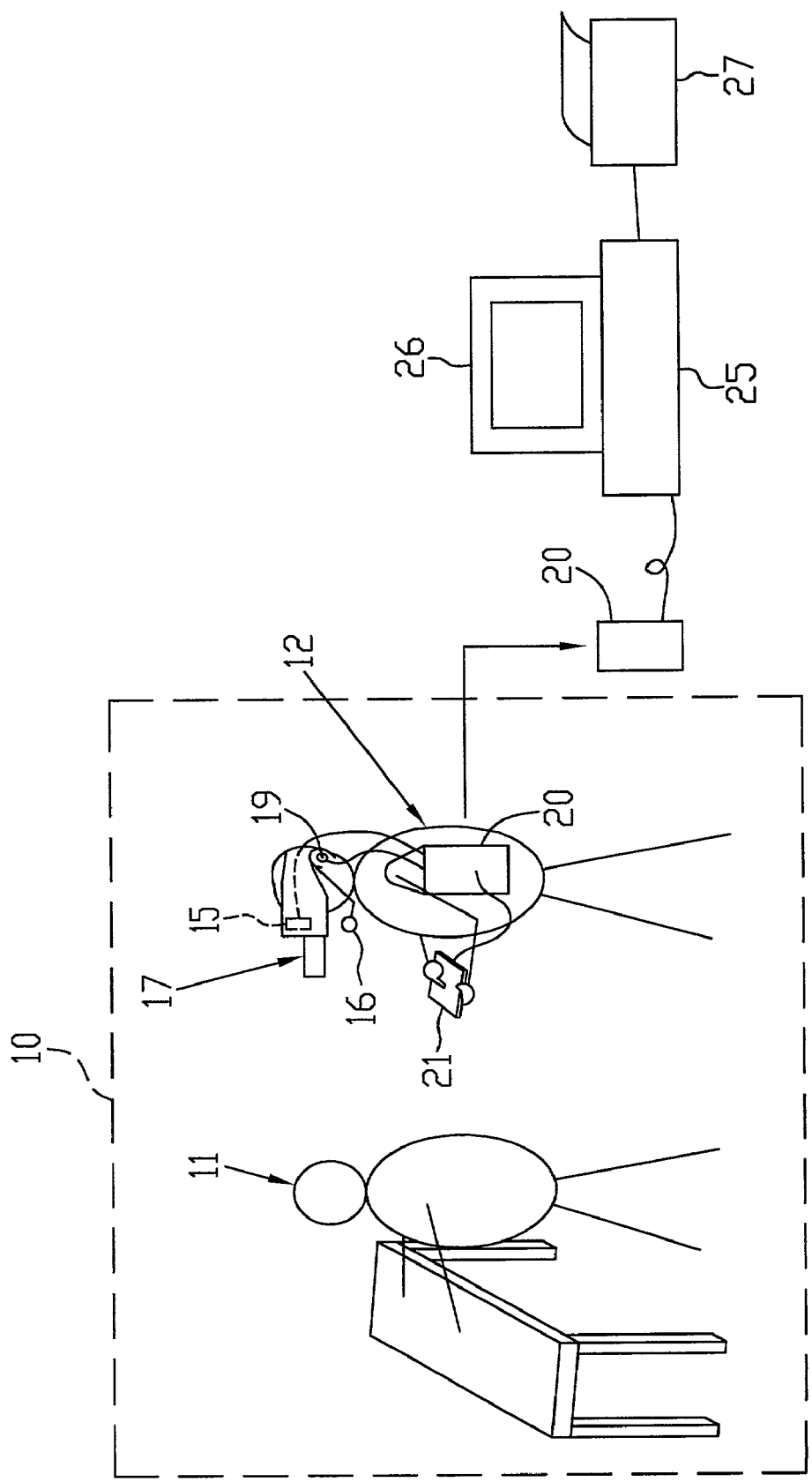
FIG. 5 is an explanatory diagram illustrating a further embodiment of the present invention, using a portable personal computer.

FIG. 5 shows an embodiment where the video camera is not utilized. In this embodiment, the data collector 12 observes the worker 11 doing the job in the darkroom 10, and looks for the title of the job on the job title list displayed on the LCD display 15. When the corresponding job title is found in the list, the data collector 12 operates the hand switch board 21 to place the cursor on that job title, and presses the enter key. Thus, at the start of each job, the job title is recorded on a hard disc or another memory device of the portable personal computer 20 along with start time data representative of the time of starting the job.

At the conclusion of each job, the data collector 12 presses the enter key while placing the cursor on the corresponding job title. Then, end time data representative of the time of finishing the job is recorded along with the job title on the memory device of the portable personal computer 20. Where a plurality of different kinds of jobs are to be carried out in success ion, the sequence of doing the respective jobs is previously checked out, and the job title of the next job is entered at the break point.

If the corresponding job title is not included in the job title list on the LCD display 15, the job title is entered as a sound signal through the microphone 16. In the light room, the data collector 12 takes of f the darkroom goggle 17 and makes the same operation as in the darkroom 10.

Figure 6:
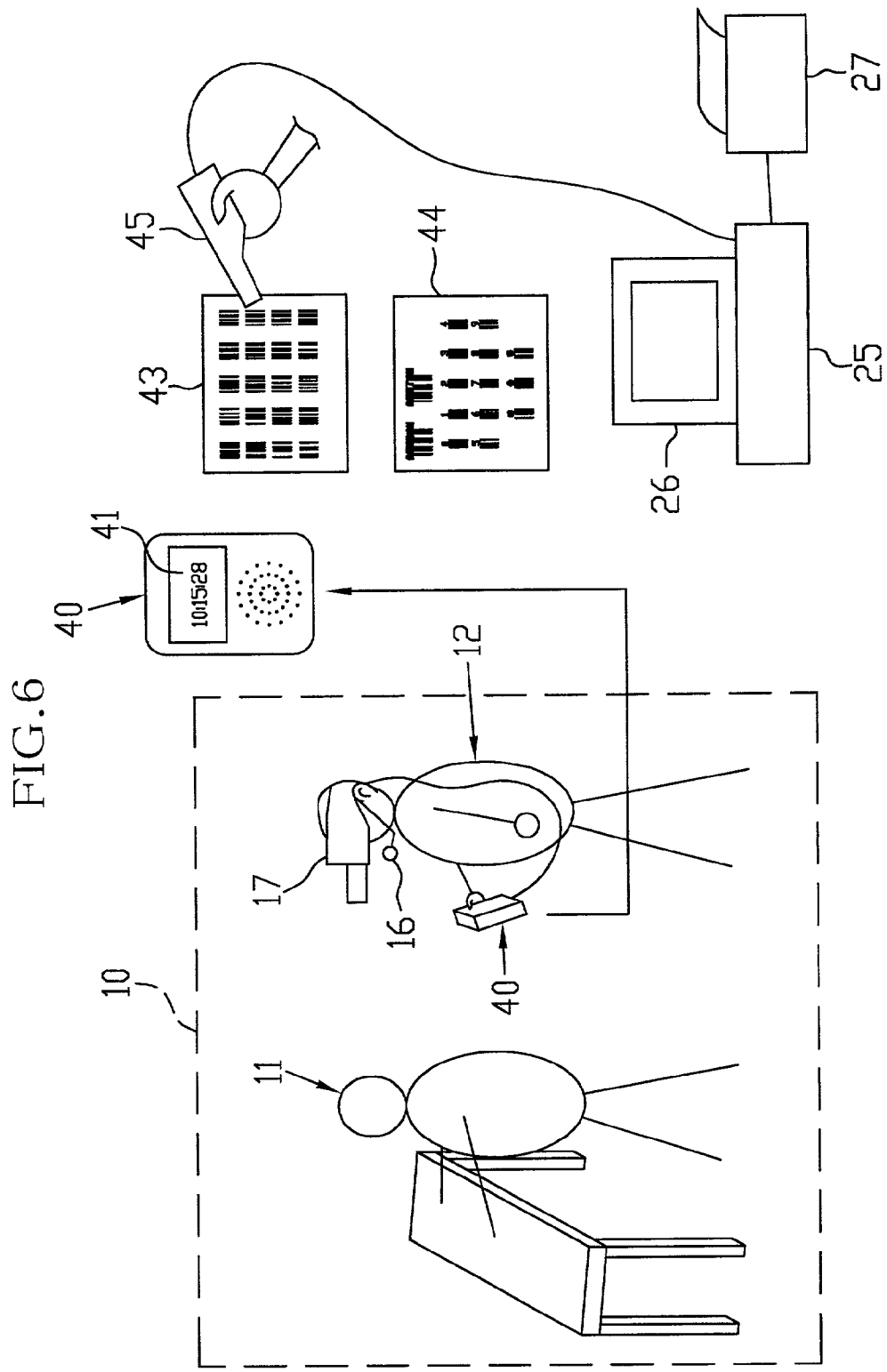
FIG. 6 is an explanatory diagram illustrating another embodiment of the present invention, using a sound recording player.

In another embodiment shown in FIG. 6, the data collector 12 uses a sound recording player 40 in place of the portable personal computer 20. When the data collector 12 tells a job title to the microphone 16 at the start and the end of one job, the job title is recorded on a memory of the sound recording player 40 along with the time when the job title is recorded. The sound recording player 40 may displays the recorded time on an LCD panel 41 when the sound recording player 40 plays back the voice telling the corresponding job title.

After the job tiles of all jobs to observe are recorded in the sound recording player 40 at respective break points between the jobs, an operator enters job title data and break point time data in the data processing personal computer 25 by use of previously prepared bar code sheets 43 and 44 and a bar code reader 45 that is connected to the data processing personal computer 25. The bar code sheet 43 has bar codes representative of different job titles, whereas the bar code sheet 44 has bar codes for entering the time data. While playing back the sound recording player 40 and listening to the job title from the speaker of the sound recording player 40, the operator enters the job title by scanning a corresponding one of the bar codes on the bar code sheet 43 with the bar code reader 45. The operator also enters the break point time data by scanning those bar codes on the bar code sheet 44 with the bar code reader 45, which correspond to the job starting time displayed on the LCD panel 41.

Figure 7:
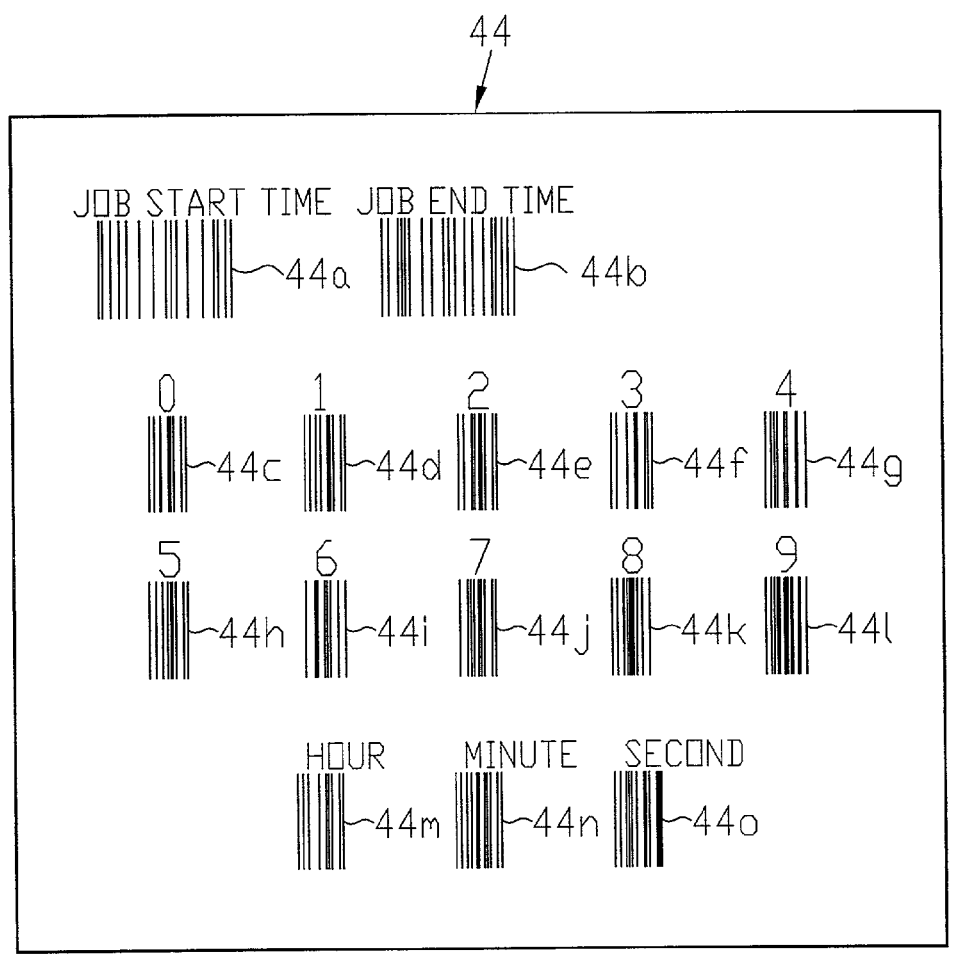
FIG. 7 is an explanatory diagram illustrating an example of bar code sheet for use in entering times.

FIG. 7 shows an example of the bar code sheet 44, that has bar codes 44a and 44b for discriminating between the job starting time and the job end time, bar codes 44c, 44d, 44e, 44f, 44g, 44h, 44i, 44j, 44k and 44l representative of numbers "1" to "9" respectively, and bar codes 44m, 44n and 44o representative of "hour", "minute" and "second" respectively. For instance, where the displayed time is "10:15:28", and it represents a starting time of one job, the operator first scans the bar code 44*a* to label the time data as job starting time data, and then seriatim scans the bar code 44*d*, the bar code 44*c* and the bar code 44*m* to enter the hour "10". Thereafter, the operator scans the bar code 44*d*, the bar code 44*h* and the bar code 44*n* to enter the minute "15", and then scans the bar code 44*e*, the bar code 44*k* and the bar code 44*o* to enter the second "28".

The bar code reader 45 may be a code-less type. In that case, data is transferred from the bar code reader 45 to the data processing personal computer 25 after the completion of scanning, by connecting the bar code reader 45 to the data processing personal computer 25 through a cable, or by use of infrared communication. It is also possible to use a signal collector that is previously connected to the data processing personal computer 25, and reads the work data from the bar code reader 45 automatically or upon a button operation when the bar code reader 45 is put on the signal connector, to transfer the work data to the data processing personal computer 25.

Instead of using the bar code sheet, it is possible to display the job titles on the display 22 of the data processing personal computer 25, for selecting appropriate ones from these job titles by means of a touch panel device or through the keyboard connected to the data processing personal computer 25. The same data collecting method as shown in FIG. 6 is applicable to work data collection in the light room, though the data collector does not use the darkroom goggles 17 in the light room.

It is alternatively possible to use different data collection methods for the darkroom and the light room. That is, work data is collected in the darkroom according to the embodiment shown in FIG. 6, using the sound recording player 40. In the light room, on the other hand, the data collector scans appropriate bar codes on the bar code sheet 43 at each break point between the jobs while observing the jobs. In that case, the bar code reader has a built-in clock, so the time when the bar code is scanned is recorded along with the corresponding work data. Thereby, the work data collected in the light room is transferred from the bar code reader to the data processing personal computer 25 through a connection wire or cable, infrared communication or the signal collecting device. So the labor for entering the work data in the data processing personal computer 25 is reduced as for the data collected in the light room.

Figure 8:
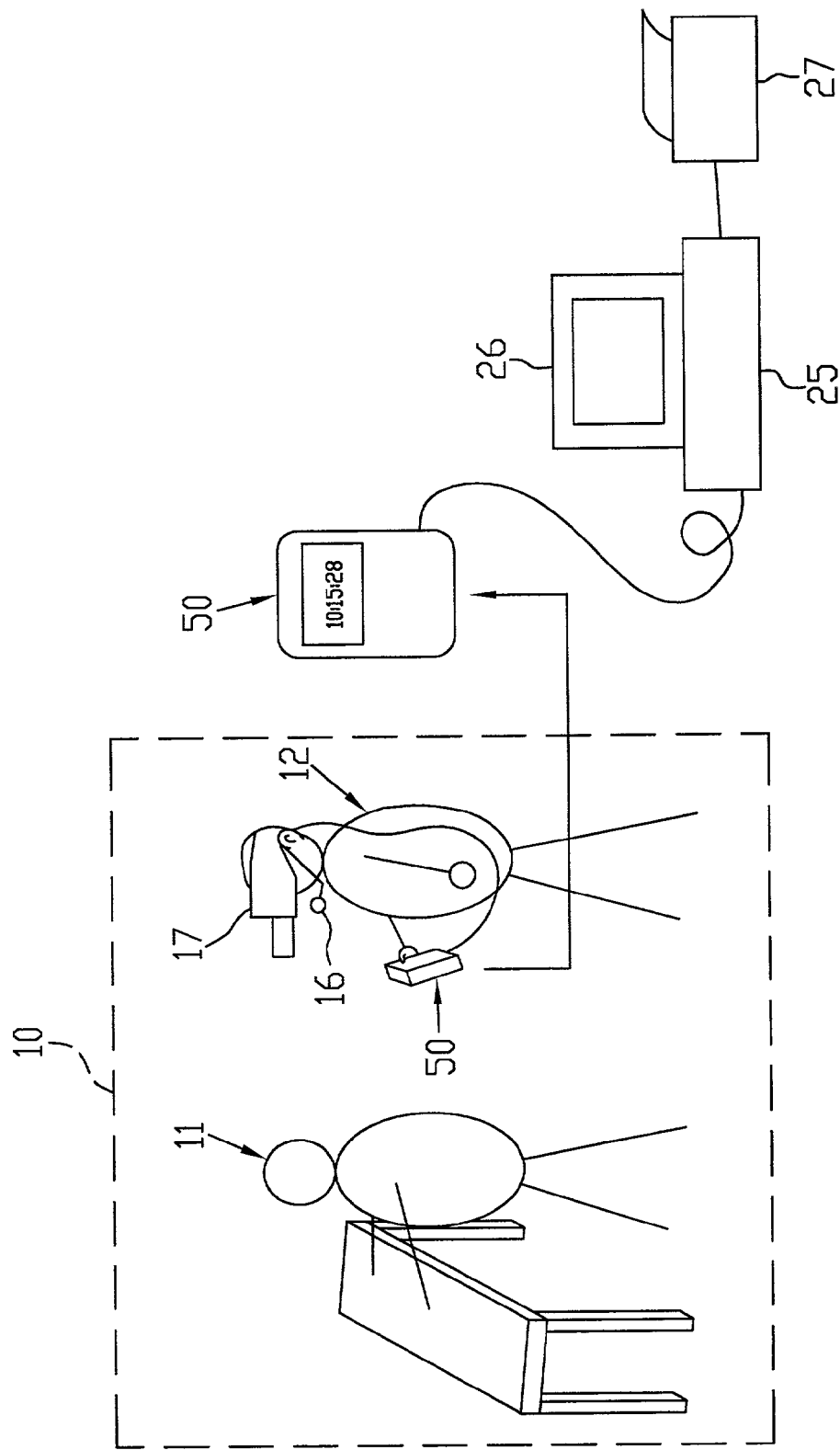
FIG. 8 is an explanatory diagram illustrating still another embodiment of the present invention, using a portable personal computer.

In a further embodiment of the invention as shown in FIG. 8, the work data is collected in through a sound recording player 50 in the same way as described with respect to the embodiment shown in FIG. 6, but the sound recording player 50 is connected to the data processing personal computer 25 through a cable, to transfer the voice data of the job titles and the time data of the break points to the data processing personal computer 25. The transferred voice data is converted into character data through an appropriate function that is provided in the data processing personal computer 25, e.g. an application package. This method is used for the light room. It is possible to transfer the data from the sound recording player 50 to the data processing personal computer 25 through infrared communication or other device than the cable.

According to another embodiment a portable personal computer with an interactive voice response system is used, wherein the data collector says a job title "X" to a microphone, then the portable personal computer retrieves the job title "X" from a job title list that is entered previously. If there is the job title "X" in the job title list, the portable personal computer repeats the job title "X". The data collector listens to the repeated voice from the portable personal computer through an earphone. When the data collector answers "YES" reply to the repeated voice at the start of each job, the job title is recorded as character data in a memory device of the portable personal computer, and the time when the job title "X" is recorded is concurrently recorded as time data of a break point.

If the said job title "X" is not registered in the job title list, the portable personal computer responds "The job title X is unlisted. Register the job title X ?" through the earphone. If the data collector says "YES" in reply, the job title "X" is added to the job title list. Thereafter when the data collector says the job title "X" again, the portable personal computer repeats the job title "X" then, so the data collector may answer "YES" at the start of that job, to let the personal computer store the job title "X" in the memory device along with the time data of that break point. Since the job titles are recorded after being confirmed in this embodiment, data input error is prevented. The same method is applicable to collecting work data in the light room. Because this embodiment may be illustrated approximately equivalently to FIG. 1, this embodiment is not illustrated in the drawings.

In an alternative, the data collector says a job title to record the job title in the sound recording player through the microphone, and thereafter turns on a voice switch of a voice clock at a break point between the jobs, to cause the voice clock to generate a voice saying the time of that break point, for recording the voice from the voice clock in the sound recording player through the microphone. It is possible to record the time of the break point prior to the job title.

Figure 9:
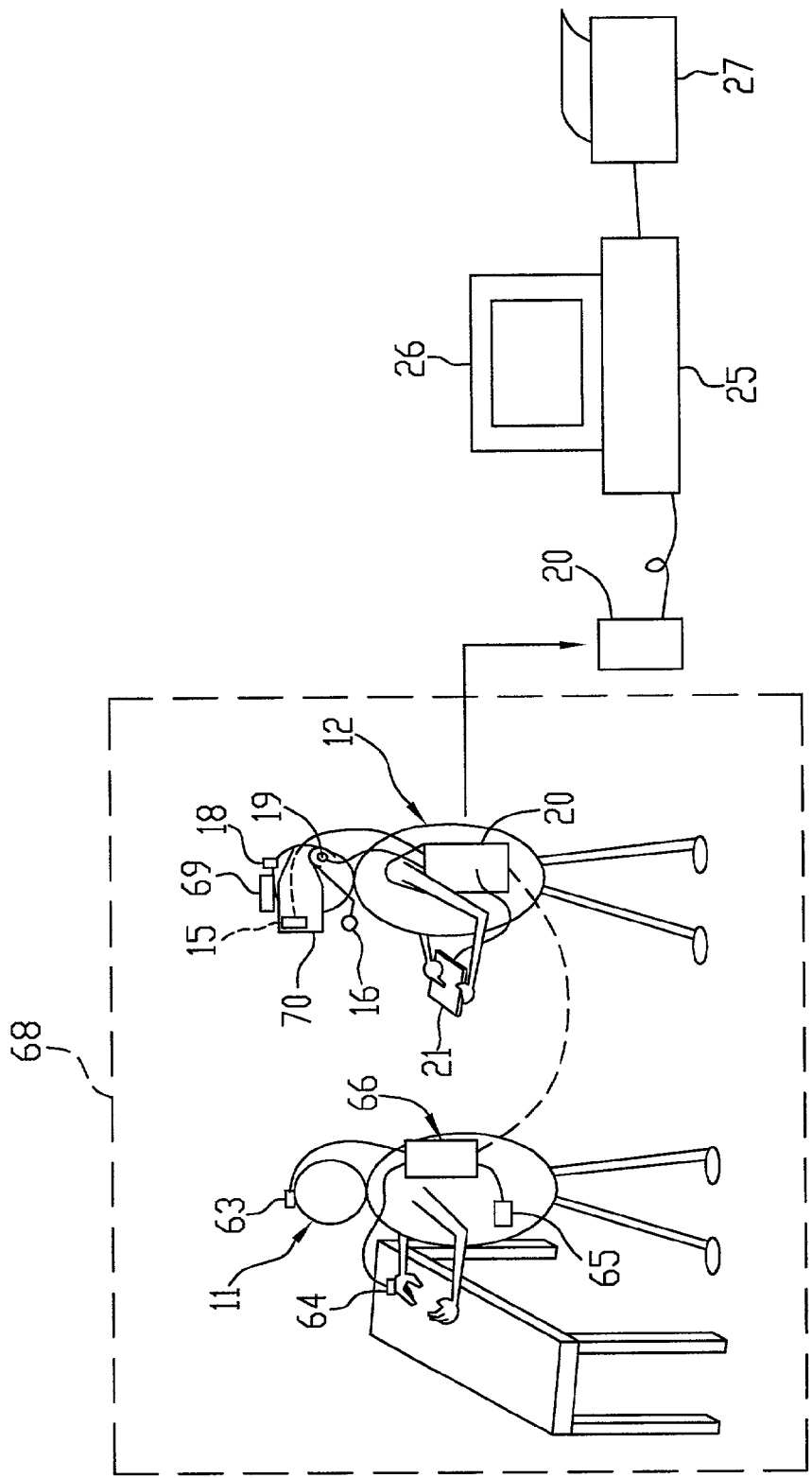
FIG. 9 is an explanatory diagram illustrating a further embodiment of the present invention, for measuring workload on a worker.

Next, an embodiment shown in FIG. 9 will be described. In this embodiment, a worker 11 is equipped with more than one biological sensor, i.e. three biological sensors 63, 64 and 65 on the head, on the back of his or her hand and on the hip in the illustrated example. Output signals from the biological sensors 63 to 65 are entered through a radio communication device 66, e.g. a blue tooth, into a portable personal computer 20. In that case, the portable personal computer 20 is equipped with a counterpart radio communication device to the radio communication device 66.

On the other hand, a data collector 12 to observe the worker 11 doing jobs has a work environment sensor 18, a very small video camera 69 and a goggle 70 on his or her head in a work area 68. An LCD display 15 is mounted inside the goggle 70, such that the data collector can look up the screen of the LCD display 15. The work environment sensor 18 may be put on the worker 11 or disposed on any appropriate locations in the work area 68, besides the data collector 12. In that case, the work environment sensor 18 remote from the data collector 12 is connected through a communication device to the portable personal computer 20. Like or equivalent elements are designated by the same reference numbers as used in the above embodiments, and the description of these elements are omitted.

For example, the biological sensors 63 to 65 are acceleration sensors that quantitatively determine the degree of workload on the basis of movements or physical displacements of the worker's head, hand and hip. Although the worker puts on only three biological sensors in the embodiment of FIG. 9, this is only for the sake of simplifying the explanation and the illustration. In practice, it is desirable for the worker to put as many biological sensors as possible on his or her body, e.g. on the shoulder, elbow, knee, ankle and so forth.

Besides the acceleration sensors, the biological sensors may be well-known gyroscopes or relative position sensors that use magnetic wave or electronic wave. A magnetic sensor for detecting relative positions of respective portions of the worker's body, or illumination sensor for measuring illuminance of the field of view may also be used as the biological sensor. According to the purpose, it is possible to use a sensor for measuring myogenic potential, pulses, heart beats, or brain wave. Besides the illuminance sensor, it is possible to use a temperature sensor, humidity sensor, gas density sensor or sound volume sensor. As for the infrared sensor that measures the body temperature, it is carried by the data collector to measure the body temperature of the remote worker. To measure the body temperature at different portions of the worker, a plurality of thermometers are put on the respective portions of the worker.

As the biological sensor, it is also possible to put a CCD camera with a super wide angle lens on the top of the worker while directing the camera upward, to calculate the direction of movement of the worker's head and the change of the direction quantitatively on the basis of image data picked up through the CCD camera. By use of data from the acceleration sensors on the worker's hand, leg and corporal portion, and data from a sensor detecting distances between these acceleration sensors, it is possible to obtain data showing the movement of the worker's body as a total, the movement of the worker's hands, the movement of the worker's legs, and which portions of the worker's body are overused.

It is known in the art that the number of blinks and winks of the worker, the movement of the eyeballs, the variation in worker's expression, the amount of movement of worker's gaze, and variation in brightness in the direction the worker is looking may be used as properties representative of worker's thinking and attention. Accordingly, it is possible to quantify data of these representative properties by photographing worker's face through a video camera.

It is also possible to provide specific marks on worker's hand, work, note book or the like, for recording whether these marks are included in designated positions in the image screen that corresponds to the field of view of the worker. Thereby, it becomes possible to record the frequency of worker's movements to look at a range around his or her hand during the respective job.

Furthermore, by providing sound volume sensors on worker's head and in the vicinity of worker's mouth, it is possible to obtain data of worker's voice and ambient sounds separately from each other, and check if any conversation is always held in the job. It is preferable to use such a data input device for the biological sensors that permits obtaining data from the worker without the need for contact with the worker, in view of the advantages that such sensors are easy to put on and take off, that data becomes less dependent on the wearing conditions of the sensors, and that mental pressure on the worker or invasion of worker's privacy from wearing the sensors are reduced. It is possible to use these non-contact type sensors in combination with contact type sensors, such as the myogenic potential sensor.

Data from the biological sensors 63 to 65 is stored in the hard disc of the portable personal computer 20 as attribution data for the respective jobs which are sectioned by the break point signals. It is possible to previously define judgement logic for comparison with threshold values and patterns that represent the degree and characteristics of the load, and stores the judgement data concurrently with the storage. For example, a preliminary observation is carried out once without setting any time limit for each job, and maximum values of the data obtained from the biological sensors on the respective jobs are defined to be the threshold values. If the data obtained in the observation on the actual job goes above the threshold value of that job, judgement data may be stored showing that the time limit for that job results a higher workload.

Figure 10:
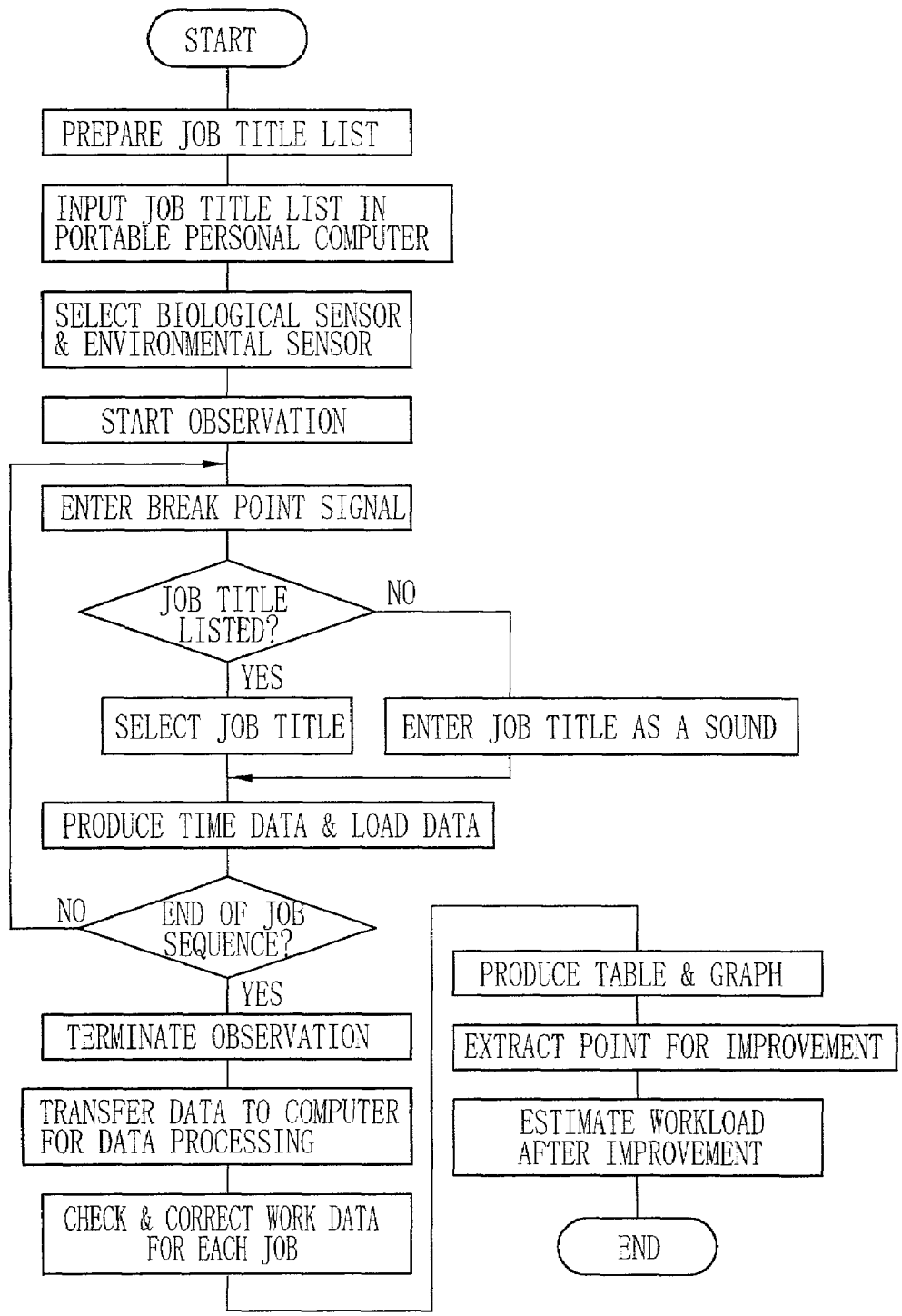
FIG. 10 is a flowchart illustrating a data collection sequence for the embodiment of FIG. 9.

Now the operation of the embodiment shown in FIG. 9 will be described with reference to the flowchart of FIG. 10.

Prior to the observation, the objects of the observation is specified, and the fineness of data to observe and other parameters are predetermined. As concrete exemplary of the objects of the observation, there would be redesigning the working process, or changing the number of workers disposed for the same job. Also the titles of jobs to observe are listed while defining the titles and classifying them according to some definition, and the job title list is input in the portable personal computer 20 in advance. In addition, according to the purpose of the analysis, it is determined what kinds of biological sensors and environment sensors should be used, what the purpose of obtaining the data, how much sensors should be placed in which locations, and how to process the data, and the portable personal computer 20 is preset correspondingly.

The data collector 12 first puts the portable personal computer 20 on the shoulder and the LCD display 15 on the head, and then puts on the darkroom goggle 17. Thereby, the LCD display 15 is covered with the darkroom goggle 17 in a light-tight fashion. Next, the data collector 12 puts the infrared video camera 14 on the head and the earphone 19 on the ear, and then turns on the portable personal computer 20. While holding the hand switch board 21 in the hand, the data collector 12 enters the darkroom 10.

The data collector 12 observes the worker 11 doing a series of different kinds of jobs, and starts photography by the video camera 69 before the worker 11 starts the series of jobs. Simultaneously with the start of the initial job of the series, the data collector 12 inputs a first break point signal by operating a signal input button on a hand switch board 21.

Thereafter, the data collector 12 looks for the title of the job photographed at that time while having the job title list displayed on the LCD display 15. When there is the corresponding job title in the list, the data collector 12 operates the pointing device on the hand switch board 21 to place the cursor on that job title, and presses the enter key. Thus, the job title is recorded along with the video data on the hard disc of the portable personal computer 20. In this way, the data collector 12 photographs the jobs by the infrared video camera 14 while inputting the break point signal and the job title at each break point between the jobs, till all the jobs in the series are done.

If the corresponding job title is not included in the job title list on the LCD display 15, the job title is entered as a sound signal through a microphone 16 at the break point for that job. The portable personal computer 20 converts the sound signal representative of the job title into character data and stores the character data along with the video data. As the video camera 69 photographs the jobs, the work environment sensor 18 measures illuminance, noise, temperature and humidity of the workplace, and enters the measured values in the portable personal computer 20. The biological sensors 63 to 65 supply the portable personal computer 20 with data of the body temperature of the worker 11, data of movements of the worker's head, hand and hip, and data obtained through the load judgement logic.

Figure 11:
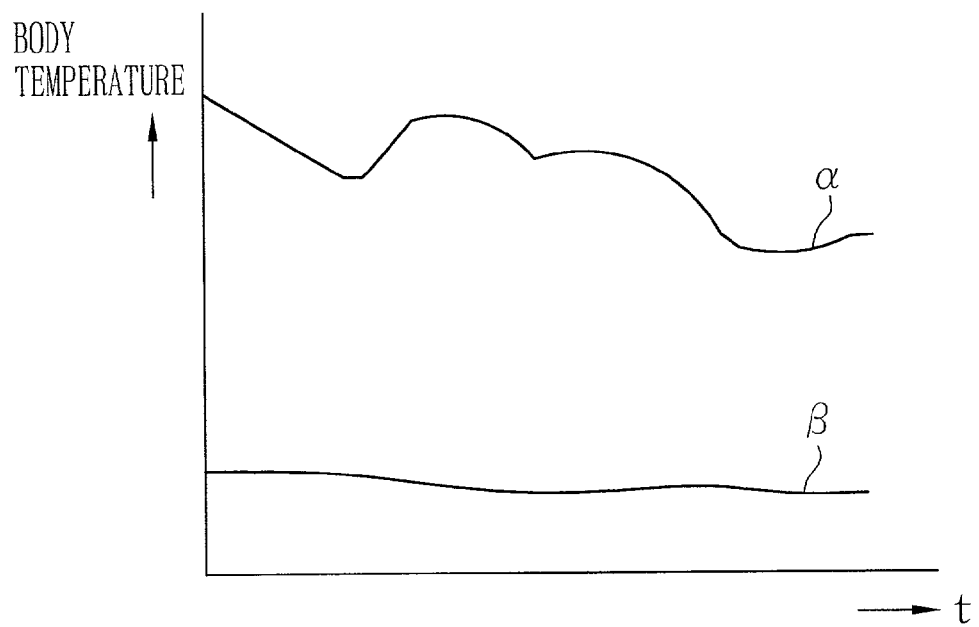
FIG. 11 is a graph illustrating changes in worker's temperature with time during the same job under different degree of restrictions on time.
Figure 12:
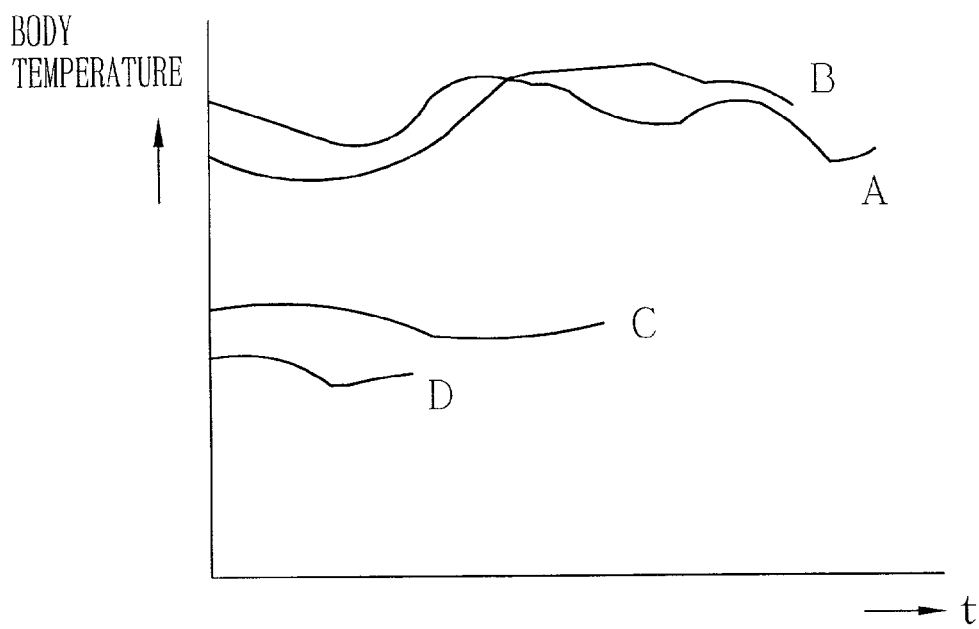
FIG. 12 is a graph illustrating changes in worker's temperature with time on different kinds of jobs.

As exemplary of the workload data, temperature data detected through an infrared sensor includes prime data $\alpha$ and $\beta$, as shown in FIG. 11, both showing changes in worker's body temperature with time during a job "A", but measured under different conditions, e.g. a large restriction on time is imposed in one case, whereas the time restriction is not so hard in the other case. The temperature data also include prime data that show changes in worker's body temperature with time during each of different jobs A, B, C and D, as shown in FIG. 12. As for the data of relative positions of the respective body portions, that is detected for example through a magnetic sensor, or the data of displacement of the respective body portions, that is detected through the acceleration sensors, prime data representative of amounts of displacement in a time section for each job, e.g. variations in position and inclination to front, rear, left, right, up and down, and mean values and maximum values of the displacements are stored. Where the workload data is illuminance data in the direction of view field, prime data representative of changes in illuminance with time during each individual job and mean values as well as maximum values are stored. If a sensor measuring the blinks and winks or the movement of the eyeballs through a camera is used as the biological sensor, variations in blinking timing, in the number of blinks and in the time interval of blinks during each job are stored as workload data.

After the completion of the observation on the jobs, the portable personal computer 20 is connected through a cable to a personal computer 25 for data processing, for transferring the work data from the portable personal computer 20 to the data processing personal computer 25. The work data may be transferred through a removable memory media, e.g. DVD or RAM. The data processing personal computer 25 transforms the work data into graphs or tables and displays the graph or table on the display 26, so as to make studies and analyses about the work time and workload for each job. If necessary, a hard copy of the work data is printed out through a printer 27.

Figure 13:
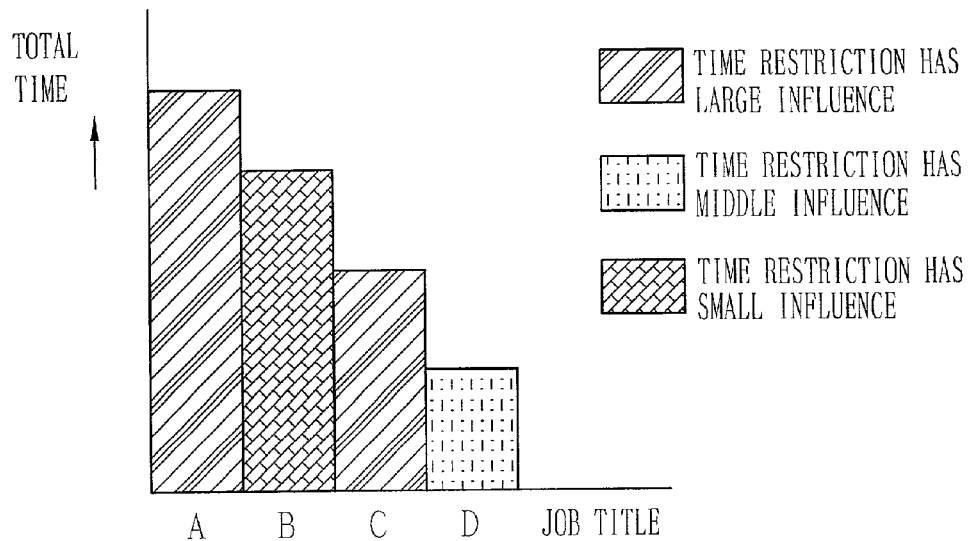
FIG. 13 is a Pareto diagram illustrating how much the time restriction has influence on the workload with respect to the different kinds of jobs.
Figure 14:
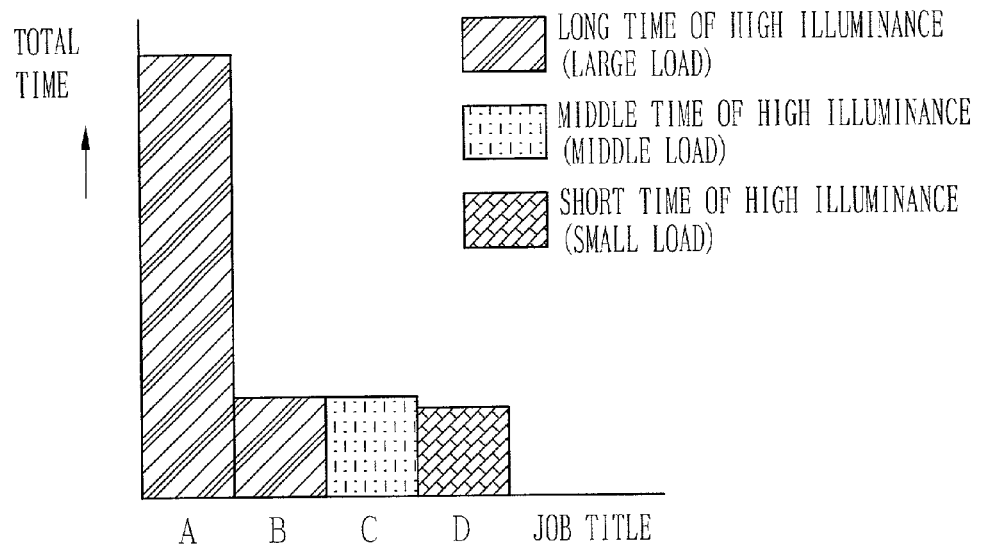
FIG. 14 is a Pareto diagram illustrating degrees of workloads with respect to the different kinds of jobs.

For analysis of the work data, the work data is tallied up for the respective jobs in a process, and the content of each job is analyzed. In the analysis for each job, it is usual for the analysis with the job title and time to use tables in which a mean time, a total time and a ratio to the total time are obtained for each job title, and a Pareto diagram in which the job titles are arranged in a sequence from the longest total time, as shown in FIG. 13. By displaying a graph showing the workload data, as shown in FIG. 14, in addition to the graph of FIG. 13, it is possible to show characteristics of the process and get priorities right for improvement in working conditions with respect to each job. According to the example shown in FIGS. 13 and 14, the job titled "A" is largely affected by the time restriction, and the illuminance in the direction of the view field is high for a longest time in this job. That is, the job "A" is to input data while staring in a CRT display with a relatively high brightness, and thus the workload is very high. On the contrary, the job "B" is not largely affected by the time restriction, and the total work time is short, through the illuminance in the direction of the view field is high. Therefore, the workload of the job "B" in total may be considered to be relatively low.

Figure 15:
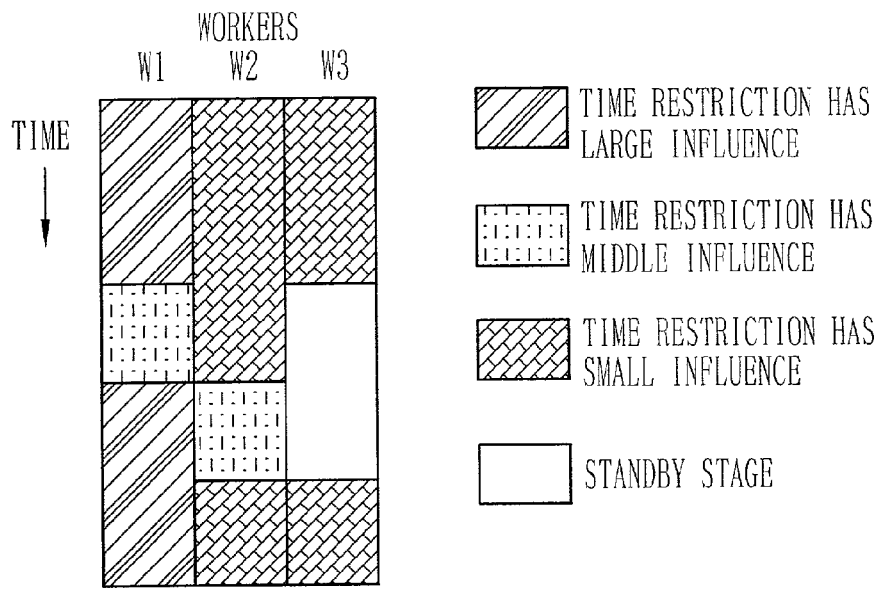
FIG. 15 is a Gantt chart illustrating time-sequences of jobs sequentially done by three workers in a limited time period, while ranking the jobs according the degree of influence of the time restriction on the workload.
Figure 16:
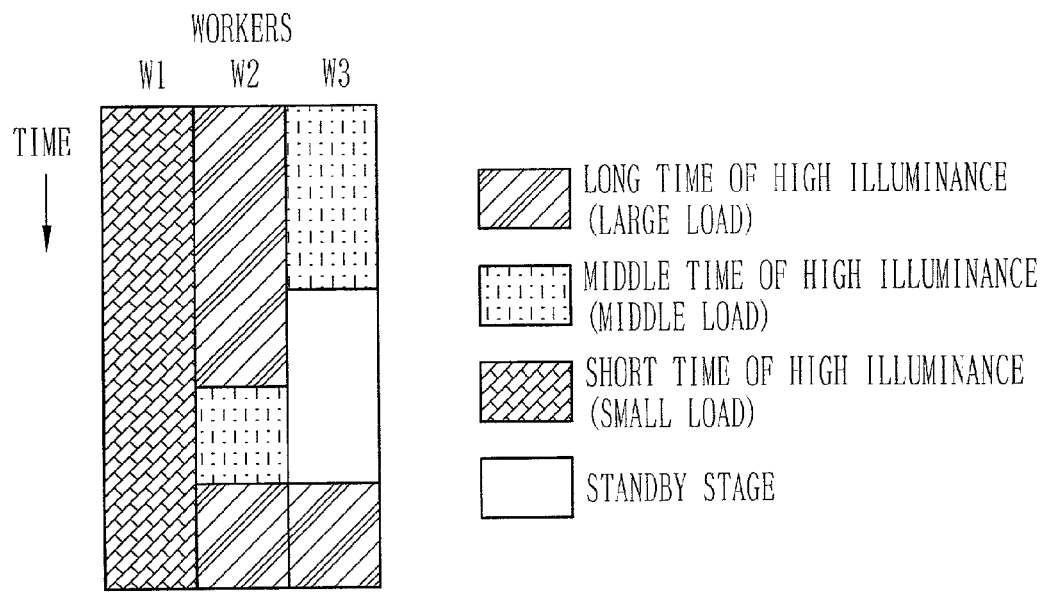
FIG. 16 is a Gantt chart illustrating time-sequences of jobs sequentially done by three workers in a limited time period, while ranking the jobs according to the degree of workload that is measured by how long the worker should look in high illuminant objects.

For analysis of job sharing and timing, it is usual to display the contents of jobs in a time sequential fashion in the form of a man-machine chart or Gantt chart, as shown in FIG. 15. By displaying a chart showing the workload data obtained by the length of high illuminance time period in the view field direction, as shown in FIG. 16, in addition to the Gantt chart, it is possible to show the viewpoints for improvement in the job sequence and shares. In these charts, the time is the work time, and the total work time is 8 hours in this instance.

According to the data analysis based on the charts shown in FIGS. 15 and 16, a worker W1 does a constant speed job, a job to be done at an approximately constant speed, in a process with heavy restriction of time, so the workload is highly dependent upon time. Since the high illuminant time in the view field direction is short, the worker's attention or carefulness is also dependent upon time. On the other hand, a worker W2 is less affected by the time restriction, but the workload on the eyes may be judged to be large in view of the data of illuminance in the view field direction. The worker W2 is presumed to be in charge of a job that requires the worker to stare in a bright object, like a display or an inspection box (Schaukasten).

Figure 17:
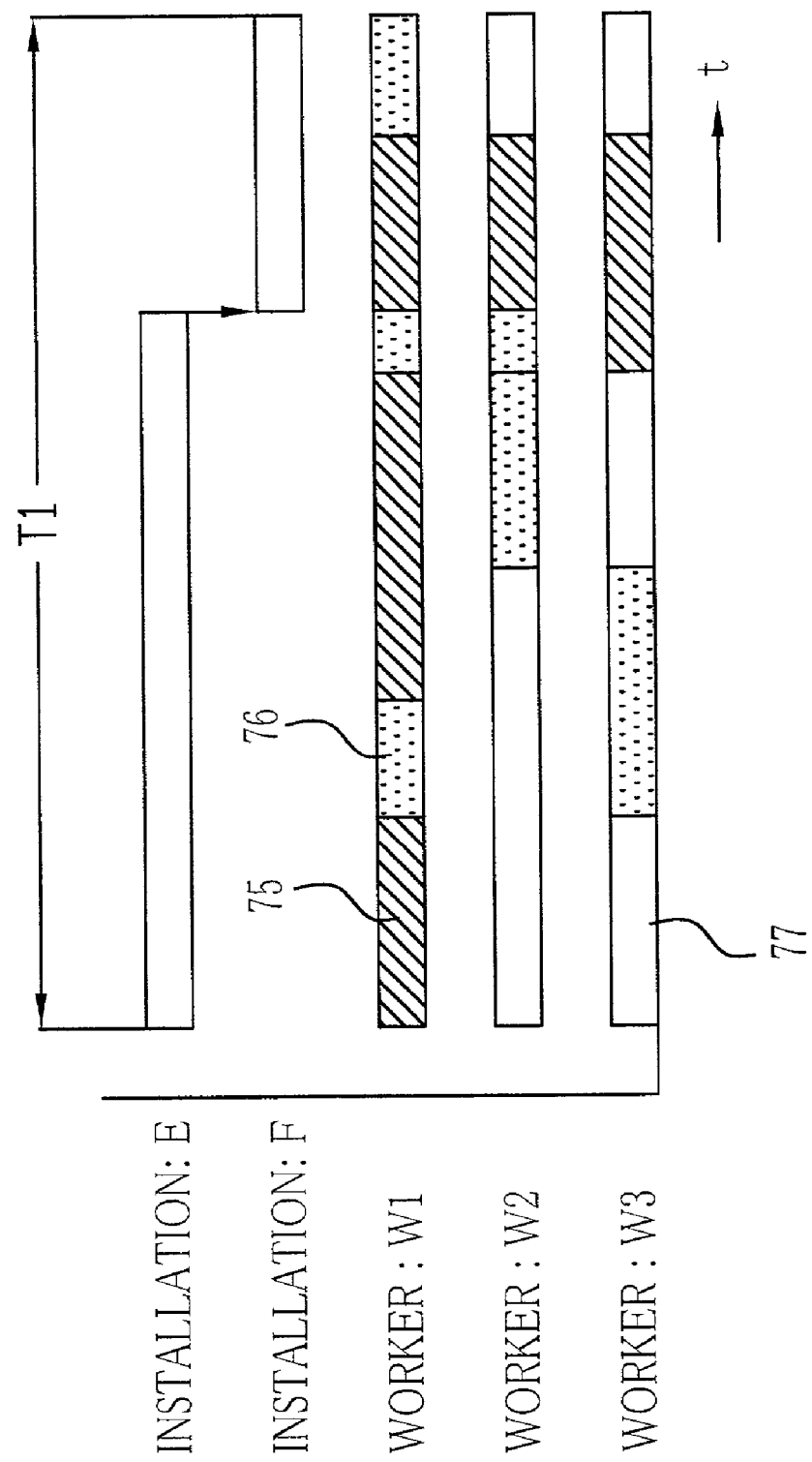
FIG. 17 is a Gantt chart illustrating restrictions on movement and on job sequence with respect to two installations.

Furthermore, by entering those data in the PERT (Program Evolution And Review Technique) software that represents restrictions applied by installations onto the movement and the sequence of jobs, so as to display workload conditions in combination, as shown in FIG. 17, it is possible to provide a Gantt chart showing the offset in work time or in workload as the results of job allocation in the process. In FIG. 17, hatched sections 75 represent jobs with relatively high workload, dotted sections 76 represent jobs with relatively low workload, and blank sections 77 represent standby state.

In the illustrated example, the worker W1, W2 and W3 do the respective jobs in an installation E during the first two third and more of a total work time T1, and then in another installation F almost during the last one third of the total work time T1. The worker W1 is busy working through the total work time T1. The worker W2 is in the standby state in the first half of the total work time T1, and starts a job with a low workload from the last half of the job in the installation E, and gets busy after shifting to the job in the installation F, but comes into the standby state in the last half of the job in the installation F. The worker W3 is in an easy condition with the standby state and the easy job during the job in the illustration A, but gets busy immediately before shifting to the installation F, and then comes to the standby state in the last half of the job in the installation F. In view of this situation, it is easy to think of an improvement that the worker W2 and W3 whose workloads have been very low can share the job of the worker W1 at least in the first half of the total work time T1. In this example, the total work time T1 is one hour.

By use of the workload data and dividing the jobs into several segments, it is also possible to express the characteristics of the process by the number of jobs and the total time in each segment. For example, standards for discrimination between large, middle and small values of the workload data about each job are determined to sort the data for each job. It is also possible to divide the data into segments by combining the data with one another, or rank the jobs by use of total indexes that are obtained by weighting the load data. Analyzing the job in this way makes it easy to find out those jobs which should be inspected and improved.

The following Table 1 shows the ranking of jobs P, Q, R and S in view of the workload, along with the work time ratio and the frequency. Table 2 and Table 3 show the work time ratio and the frequency of the workloads of the respective ranks, with respect to different workers W1 and W2.

TABLE 1

| JOB | P | Q | R | S |
|---|---|---|---|---|
| INFLUENCE OF TIME RESTRICTION | LARGE | LARGE | MIDDLE | MIDDLE |
| LOAD ON EYES | LARGE | MIDDLE | MIDDLE | SMALL |
| MOVEMENT OF EYEBALLS | LARGE | MIDDLE | MIDDLE | MIDDLE |

TABLE 1-continued

| JOB | P | Q | R | S |
|---|---|---|---|---|
| MOVEMENT OF WORKER | SMALL | LARGE | MIDDLE | MIDDLE |
| MOVEMENT OF WORKER'S HAND | LARGE | LARGE | MIDDLE | SMALL |
| WORK TIME | 100 | 90 | 50 | 40 |
| FREQUENCY | 4 | 2 | 7 | 3 |
| TOTAL INDEX | 90 | 40 | 35 | 15 |

TABLE 2

[WORKER W1]

| | INFLUENCE OF TIME RESTRICTION ||||||||| 
|---|---|---|---|---|---|---|---|---|---|
| | LARGE ||| MIDDLE ||| SMALL |||
| LOAD ON EYES | L | M | S | L | M | S | L | M | S |
| WORK TIME | 100 | 80 | 60 | 50 | 250 | 300 | 30 | 500 | 600 |
| FREQUENCY | 2 | 4 | 2 | 5 | 25 | 10 | 20 | 50 | 60 |

TABLE 3

[WORKER W2]

| | INFLUENCE OF TIME RESTRICTION |||||||||
|---|---|---|---|---|---|---|---|---|---|
| | LARGE ||| MIDDLE ||| SMALL |||
| LOAD ON EYES | L | M | S | L | M | S | L | M | S |
| WORK TIME | 0 | 60 | 60 | 10 | 50 | 30 | 10 | 900 | 600 |
| FREQUENCY | 0 | 1 | 2 | 5 | 25 | 10 | 20 | 10 | 60 |

In this way, characteristics of the job may be compared and analyzed with respect to each process or with respect to each worker, for the sake of distributing or equalizing the workload on the workers, or examining how to assign the jobs to the workers according to their skills, or setting goals for improvement in job quality.

For instance, because the data is previously sectioned by each job in Table 1, it is easy to pick up only those data which relate to the aimed job from among the data of all jobs. If there are a plurality of data pieces for the same job title, these data pieces may be compared to each other or tallied up. For example, for such job where the workload vary at each execution, it becomes possible to restructure the job procedures to stabilize the workload.

As for those jobs which are determined to be aimed at by the statistic analysis of the data on the above all jobs, more detailed analysis of the data on each of these jobs is useful for examining the object. For example, as for the job P in Table 1, the starting time, the ending time, the requisite time duration, changes or progresses in movements of respective portions of the worker's body, direction of the movements, mean values and maximum values of the moved amounts, changes with time in illuminance in the view field direction, a mean value and a maximum value of the illuminance, changes with time in body temperature in the view field direction, a mean value and a maximum value of the body temperature, and other data are shown in a lookup table. Based on the lookup table, it is possible to analyze how the workloads in the job P affect the worker, and find out necessary points for improvements in the facilities or in the working method, including job collaboration.

Specifically, it becomes possible to eliminate, combine, rearrange and simplify the jobs by optimizing load allocation during the work time and among respective workers in a collective work, by optimizing job allocation to unskilled workers, by extracting problems in calculating wages per unit job, in frequency of the workload, and in the progress of the workload with time, and by applying such viewpoints for improvement that is a kind of Industrial Engineering (IE) to examining the workloads.

Figure 18:
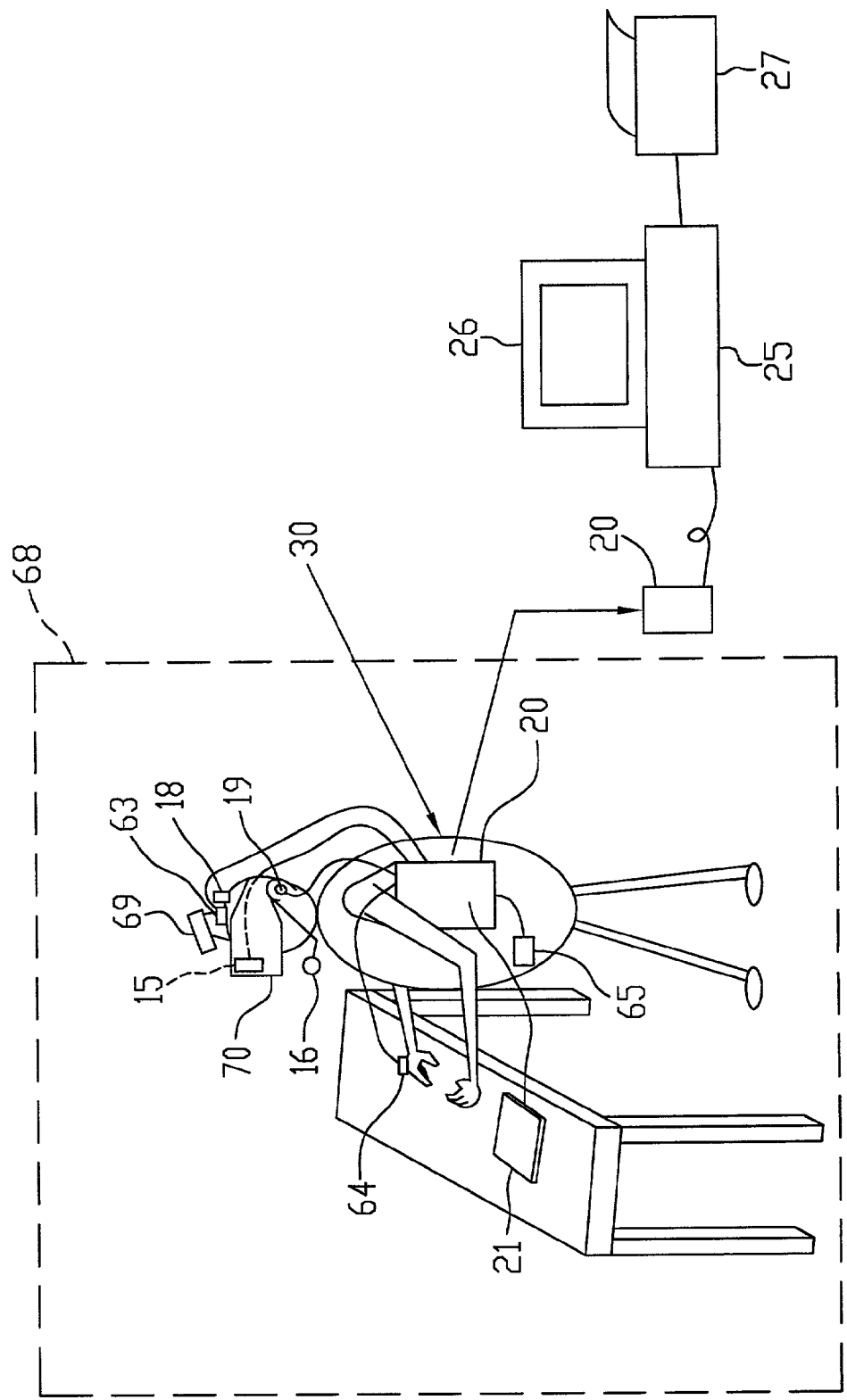
FIG. 18 is an explanatory diagram illustrating a further embodiment of the present invention, where a worker doubles as a data collector, and collects biological data on one's own body.

FIG. 18 shows a modification of the embodiment as set forth above with reference to FIGS. 9 to 17, wherein the data collector is not disposed in the work area 68, but a worker doubles as a data collector 30, carrying the video camera 69, the biological sensors 63 to 65 and other devices necessary for data collection on his or her own body. This embodiment contributes to saving labor for data collection.

Although the break point signal is entered by means of the hand switch board in the above embodiment, it is possible to predetermine the break point as a time when a particular mark comes in the view field, or by a particular sound from an installation during the process, so that the break point signal may be automatically entered. This embodiment allows to substitute a robot or the like for the data collector 12.

It is not always necessary to actuate the environment sensor and the biological sensors in cooperation with the video camera, but these sensors may operate independently. Although the workload is measured through the biological sensor in the above embodiments, the data collector may judge the degree of the workload on the worker from the observation, and input the degree of the workload through an appropriate data input device, such as a bar code reader in the workplace or while observing the photographed video pictures afterward. In the latter case, another person may judge the degree of the workload instead of the data collector.

As the video camera for the darkroom, a high-sensitive video camera like an image intensifier camera is usable instead of the infrared video camera. By attaching a special filter that changes the sensitive wavelength range of the video camera, or by using a special video camera that may switch the sensitive range between the infrared range and the visible light range, the same video camera may be used both for the darkroom and the light room.

Figure 19:
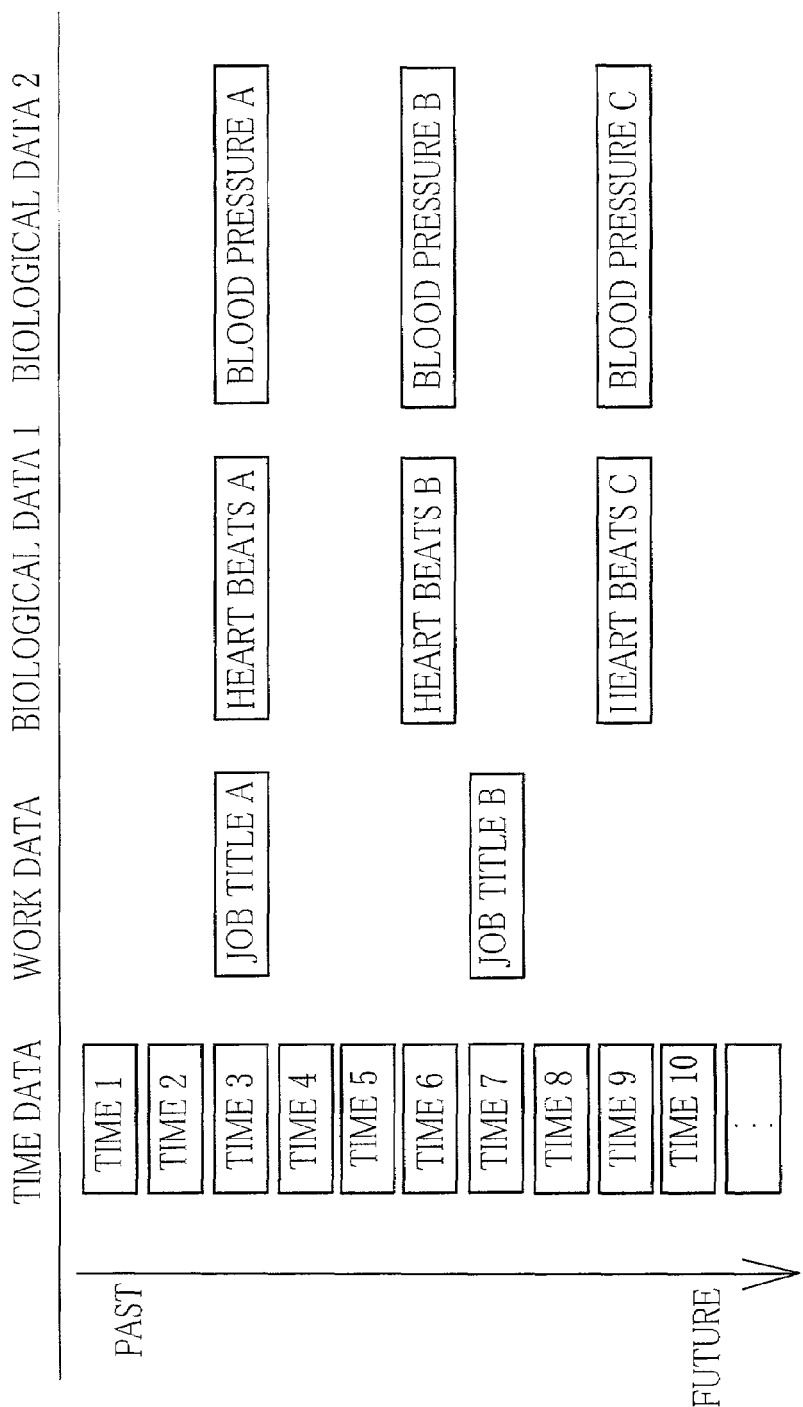
FIG. 19 is an explanatory diagram illustrating a relationship between time data and biological data.

FIG. 19 shows a method of writing the break point signal along with the time data, wherein the break point signal is recorded in association with time data that represents the time proximate to the time when the signal is entered. For example, the time data is recorded in addition to a job title or job title data. Thereby, it come to be possible to output a Pareto diagram or the like promptly from the data processing computer without the need for any manual operation. Recording image data obtained by photographing the job with the job title and the time data makes it possible to compare and investigate the content of the job and the job title in a short time by decimating the image data at appropriate time intervals. It is desirable to record the biological data in association with those data. Associating the biological data with the time data makes it possible to compare the work load in the morning with that in the afternoon, and thus allocate and schedule the jobs with regard to age and sex.

It is preferable to connect the observing apparatus, the data recording apprutus and the data processing computer to a network, so as to collect the job data. In an embodiment shown in FIG. 20, a data processing computer 101 is connected to a camera 102 with a video recording device, a portable computer 103, a monitor 104, a biological sensor 105, a hand switch 106 and a data recording device 107. The network may at least be constituted of a single data processing computer 101 and a single biological sensor 105 as an observing device. The network may otherwise be constituted of a single data recording device 107 and a single biological sensor 105. The network may be the Internet, or an intranet.

It is possible to omit the data recording device 107 and record the work data to a video cassette recorder (VCR) or the portable computer 103.

FIG. 21 shows an embodiment wherein the respective devices are connected to the network through a radio communication system. A radio LAN card 110 is attached to each of a camera 102a, a portable computer 103, a monitor 104, a biological sensor 105, a hand switch 106 and a data recording device 107. These devices are connected to the network 100 via a radio server 112 or a router. The server may be connected to an already installed office intranet or the like, so as to permit exchanging data through the intranet. Then the data processing computer may be placed in the same factory or at the department of IE engineers, and the data processing may be carried out on the data processing computer substantially in a real time fashion. The server may also be connected to the Internet. Then, even if the data processing computer is located in a remote place, e.g. abroad, it becomes possible to check the collected observation data and process the data in a real time fashion. Since there is a technique for connecting apparatuses directly to the network without the server, it is possible to connect the above devices to the network by use of this technique. The network 100 may be of a DSL standard type or an optical fiber type. Standardizing the network 100 in this way makes it possible to observe the image data along with the job title data on a remote monitor in a real time fashion.

Figure 20:
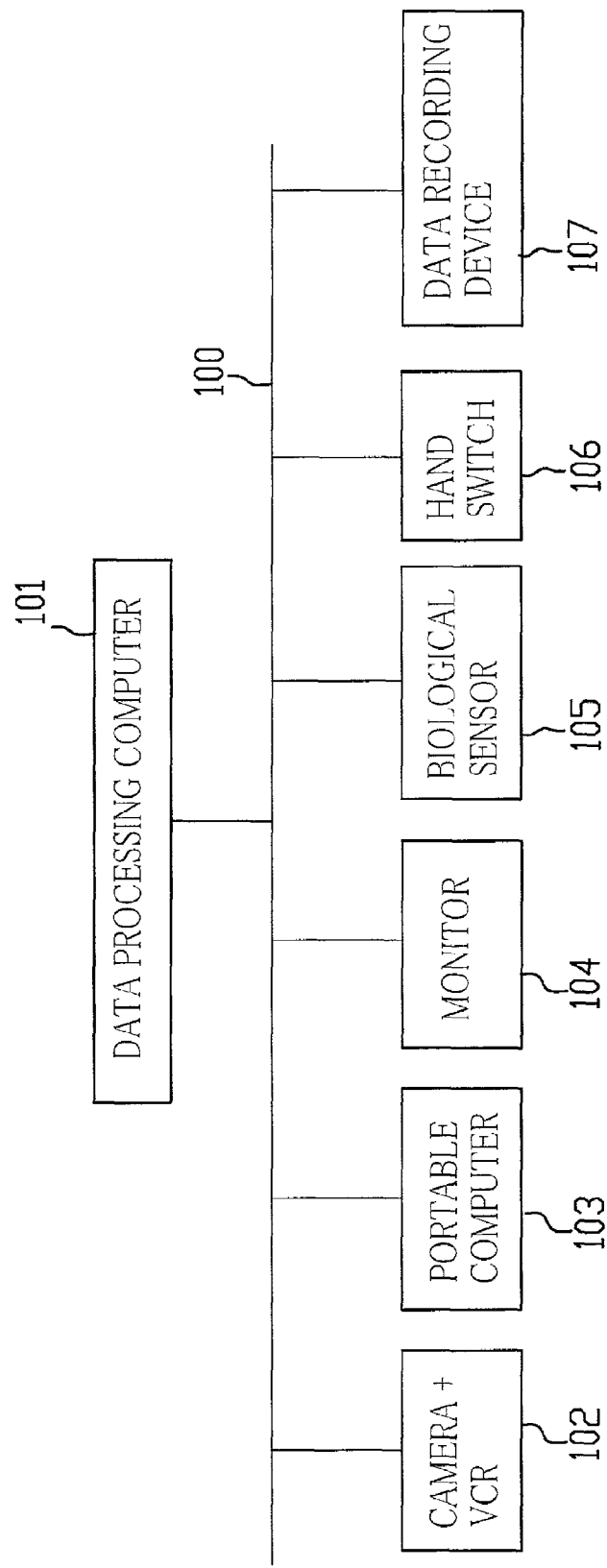
FIG. 20 is an explanatory diagram illustrating an example of networking.

In the embodiments shown in FIGS. 20 and 21, time data are recorded to the data recording device 107 at predetermined appropriate time intervals. In association with the time data, the data recording device 107 records picture signals from the camera 102 or 102a, like those of a still image, job title data or job title code data from the hand switch 106 or the portable computer 103, and data from the biological sensor 105. Concretely, the picture signal or the job title signal are written along with the time data representative of the time proximate to the entrance time of that signal. The proximate time may be slightly earlier or later than the entrance time. The data processing computer 101 reads in the time data and the biological data from the data recording device 107 in correspondence with the job title or job title code data, and produces a graph from these data.

In the above embodiments, the memory medium of the sound recording player is a high-speed accessible memory. But a hard disc or a recording tape or MD (Mini Disc) is usable instead. The present invention is applicable to those cases where the worker deals with chemical products or the like, if only the portable personal computer or sound recording player and other apparatuses as used in the darkroom in the above embodiments are provided with waterproof functions. The present invention is applicable not only to the above described observation on working conditions, but also to recording and analyzing the present conditions or modifications of the equipment in a darkroom. It is also possible to apply the present invention to worker's daily report, recording of worker's movement, recording and analyzing a conference or meeting.

Thus, the present invention is not to be limited to the above embodiments but, on the contrary, various modifications will be possible to those skilled in the art without departing from the scope of claims attached hereto.

What is claimed is:

1. A work data collection method comprising the steps of:
photographing a series of different jobs done by at least a worker through a video camera, to take video signals of said jobs;
recording said video signals of said jobs while recording time signals generated at predetermined fixed intervals;
inputting a break point signal in said video camera at each break point between said jobs;
recording said break point signal on a memory device along with said video signals and a proximate one of said time signals that is representative of a time proximate to said break point;
measuring workload on said worker during at least one of said jobs through at least one biological sensor that measures a biological factor of said worker, to take data of said workload; and
recording said workload data on said memory device in association with said video signal, said break point signal and said proximate time signal.

2. A work data collection method as recited in claim 1, further comprising the steps of inputting, said video signal, said break point signal and said proximate time signal in a personal computer, to record said video signal and said break point signal on said memory device in association with said proximate time signal through said personal computer.

3. A work data collection method as recited in claim 1, wherein said break point signal is used as a cueing signal for use in reproducing said video signals or said biological data.

4. A work data collection method as recited in claim 1, wherein said biological sensor comprises at least one of a temperature sensor, a perspiration sensor and an acceleration sensor.

5. A work data collection method as recited in claim 1, further comprising outputting a relationship between said at least one of jobs and said measured workload for analysis.

6. A work data collection method as recited in claim 5, wherein said outputted relationship is expressed in graphical form.

7. A work data collection method as recited in claim 1, wherein said break point signal comprises a signal which is searchable by a video player.

8. A work data collection method comprising the steps of:
photographing a series of different jobs done by at least a worker through a video camera, to take video signals of said jobs;
recording said video signals on a memory device through a personal computer, while recording time signals generated at predetermined fixed intervals;
inputting a break point signal in said personal computer at each break point between said jobs, to record said break point signal on said memory device along with said video signal and a proximate one of said time signals that is representative of a time proximate to said break point;
measuring workload on said worker during at least one of said jobs through at least one biological sensor that measures a biological factor of said worker; and
inputting data of measured workload in said personal computer, to record said workload data on said memory device in association with said video signals, said break point signal and said proximate time signal.

9. A work data collection method as recited in claim 8, further comprising the steps of:
  measuring environmental factors around said worker during at least one of said jobs; and
  inputting data of said environmental factors in said personal computer, to record said environmental data in association with said video signals or said break point signal and said proximate time data on said memory device.

10. A work data collection method as recited in claim 9, wherein said break point signal is used as a cueing signal for use in reproducing said video signals or said environmental data.

11. A work data collection method as recited in claim 9, wherein said work environment condition comprise at least one of illumination, noise, temperature and humidity.

12. A work data collection method as recited in claim 8, wherein said break point signal is entered as a sound signal or an image signal.

13. A work data collection method as recited in claim 12, wherein said time signals are recorded along with said video signals, and are entered as digital data in a computer, to record said break point signal or said image signals or said sound signal along with said proximate time data in said computer.

14. A work data collection method as recited in claim 8, further comprising the steps of inputting job titles or job title code data that represent kinds of respective ones of said jobs into said video camera or said personal computer simultaneously with said break point signals, to record said job titles or said job title code data in association with said break point signals.

15. A work data collection method as recited in claim 8, wherein said video camera is an infrared video camera.

16. A work data collection method comprising the steps of:
  generating time data at predetermined fixed intervals from a personal computer;
  displaying predetermined job titles on a display device connected to said personal computer, said display device being visible for a data collector while observing a series of different jobs done by at least a worker;
  selecting one of said displayed job titles through an input device connected to said personal computer, to enter job title data or job title code representative of said selected job title in said personal computer at each break point between said jobs;
  recording said job title data or said job title code on a memory device of said personal computer, along with one of said time data that is representative of a time proximate to the time when said job title data is entered;
  measuring workload on said worker during at least one of said jobs through at least one biological sensor that measures a biological factor of said worker; and
  inputting data of measured workload in said personal computer, to record said workload data on said memory device in association with said video signals, said break point signal and said proximate time signal.

17. A work data collection method as recited in claim 16, wherein said display device is an image display device that projects an image directly onto retinas of said data collector.

18. A work data collection method comprising the steps of:
  generating time signals at predetermined fixed intervals from a personal computer;
  entering a job title or a code of said job title as a sound signal through a microphone connected to said personal computer at each break point between different jobs while said jobs are being sequentially done by at least a worker;
  converting said sound signal into character data representative of said job title by said personal computer;
  recording said character data as job title data on a memory device of said personal computer, along with one of said time signals that is representative of a time proximate to an entrance time when said sound signal is entered;
  measuring workload on said worker during at least one of said jobs through at least one biological sensor that measures a biological factor of said worker; and
  inputting data of measured workload in said personal computer, to record said workload data on said memory device in association with said video signals, said break point signal and said proximate time signal.

19. A work data collection method comprising the steps of:
  letting an observer input a job start time when a worker starts a respective one of a series of different jobs;
  detecting data of physical load on said worker automatically through a biological sensor during said respective job; and
  recording said load data on a memory device along with time data generated at predetermined fixed intervals.

20. A work data collection method as recited in claim 19, wherein said biological sensor comprises at least one of a body temperature sensor, a perspiration sensor, an acceleration sensor, a gyroscope and a relative position sensor.

21. A work data collection method as recited in claim 19, further comprising outputting a relationship between said respective job and said measured data of physical load for analysis.

22. A work data collection method as recited in claim 21, wherein said outputted relationship is expressed in graphical form.

23. A work data collection method comprising the steps of:
  obtaining video signals from observation devices, and data from a biological sensor that measure a biological factor of a worker;
  inputting said video signals and said data of said biological sensor and job titles or job title code data in a recording device while inputting time data at predetermined fixed intervals, separated by break signals, in said recording device; and
  reading from said recording device said time data corresponding to said job titles or said job title code data and said data of said biological sensor into a data processing computer, to produce a designated kind of data on said data processing computer in association with said video signals, said break point signal and said proximate time signal.

24. A work data collection method as recited in claim 23, wherein said biological sensor comprises at least one of a body temperature sensor, a perspiration sensor, an acceleration sensor, a gyroscope and a relative position sensor.

25. A work data collection method as recited in claim 23, wherein said observation device, said recording device and said data processing computer are connected to the Internet, for data exchange with each other.

26. A work data collection method as recited in claim 25, wherein radio communication device is used for communication between said observation device and a server or a router that is connected to said Internet.

27. A work data collection method, wherein at least an observation device comprising at least one of a work environment sensor and a biological sensor, a recording device and a data processing computer are connected to a network, for data exchange with each other, and wherein said observation device includes at least one biological sensor that measures a biological factor of a worker;

wherein said recording device records data from the observation device, and corresponding time signals and break point signals; and wherein a designated kind of data is produced on said data processing computer in association with said video signals, said break point signal and said proximate time signal.

28. A work data collection method as recited in claim 27, wherein said data processing computer and at least an observation device are linked to said network.

29. A work data collection method as recited in claim 27, wherein said data recording device and at least an observation device are linked to said network.

30. A work data collection method as recited in claim 27, wherein said network is the Internet.

31. A work data collection method as recited in claim 27, wherein a radio communication device is used for communication between said observation device and a server or a router that is connected to said network.

32. A work data collection method as recited in claim 27, wherein said work environment condition comprise at least one of illumination, noise, temperature and humidity.

33. A work data collection method comprising the steps of:

photographing a series of different jobs done by at least a worker through an infrared video camera, to take video signals of said jobs;

recording said video signals of said jobs while recording time signals generated at predetermined fixed intervals;

inputting a break point signal in said infrared video camera at each break point between said jobs; and recording said break point signal on a memory device along with said video signals and a proximate one of said time signals that is representative of a time proximate to said break point.

34. A work data collection method according to claim 33, wherein said observation device, said recording device and said data processing computer are connected to a network, for data exchange with each other, and wherein said observation device is an infrared video camera.

35. A work data collection method comprising the steps of:

photographing a series of different jobs done by at least a worker through an infrared video camera, to take video signals of said jobs;

recording said video signals on a memory device through a personal computer, while recording time signals generated at predetermined fixed intervals; and inputting a break point signal in said personal computer at each break point between said jobs, to record said break point signal on said memory device along with said video signal and a proximate one of said time signals that is representative of a time proximate to said break point.

36. A work data collection method comprising the steps of:

photographing a series of different jobs done by at least a worker through a video camera, to take video signals of said jobs;

recording said video signals on a memory device through a personal computer, while recording time signals generated at predetermined fixed intervals;

inputting a break point signal in said personal computer at each break point between said jobs, to record said break point signal on said memory device along with said video signal and a proximate one of said time signals that is representative of a time proximate to said break point, said video camera and said personal computer are connected to the Internet, for data exchange with each other.

37. A work data collection method comprising the steps of:

photographing a series of different jobs done by at least a worker through a video camera, to take video signals of said jobs;

recording said video signals on a memory device through a personal computer, while recording time signals generated at predetermined fixed intervals;

inputting a break point signal in said personal computer at each break point between said jobs, to record said break point signal on said memory device along with said video signal and a proximate one of said time signals that is representative of a time proximate to said break point, wherein said video camera and said personal computer are connected to the network, for data exchange with each other, and wherein radio communication device is used for communication between said video camera and a server or a router that is connected to said network.

* * * * *